(12) United States Patent
Kim et al.

(10) Patent No.: US 12,295,978 B2
(45) Date of Patent: May 13, 2025

(54) RECOMBINANT PLASMA MEMBRANE-BASED VESICLE, FOR TREATING CANCER

(71) Applicant: SHIFTBIO INC., Seoul (KR)

(72) Inventors: Gi-Beom Kim, Seoul (KR); Yoo Soo Yang, Seoul (KR); In-San Kim, Seoul (KR); Gihoon Nam, Seoul (KR)

(73) Assignee: SHIFTBIO INC., Seoul (KR)

( * ) Notice: Subject to any disclaimer, the term of this patent is extended or adjusted under 35 U.S.C. 154(b) by 1387 days.

(21) Appl. No.: 16/967,074

(22) PCT Filed: Sep. 28, 2018

(86) PCT No.: PCT/KR2018/011504
§ 371 (c)(1),
(2) Date: Aug. 3, 2020

(87) PCT Pub. No.: WO2019/066535
PCT Pub. Date: Apr. 4, 2019

(65) Prior Publication Data
US 2021/0106632 A1    Apr. 15, 2021

(30) Foreign Application Priority Data
Sep. 28, 2017  (KR) .................. 10-2017-0126202

(51) Int. Cl.
*A61K 35/766* (2015.01)
*A61K 45/06* (2006.01)
*A61P 35/00* (2006.01)
*C07K 16/28* (2006.01)

(52) U.S. Cl.
CPC ............ *A61K 35/766* (2013.01); *A61K 45/06* (2013.01); *A61P 35/00* (2018.01); *C07K 16/2827* (2013.01); *C07K 16/2863* (2013.01)

(58) Field of Classification Search
CPC ............................... A61K 35/766; A61K 45/06
USPC ............................................... 424/93.2
See application file for complete search history.

(56) References Cited

U.S. PATENT DOCUMENTS 9,770,487 B2 *  9/2017  Sahin .................. A61K 31/7068
9,856,320 B2 *  1/2018  Cogswell .............. A61P 43/00

OTHER PUBLICATIONS

Harrison et al., "Viral membrane fusion". Nat Struct Mol Biol 15, 690-698 (2008). (Year: 2008).*
Dudek et al., "Inducers of immunogenic cancer cell death". Cytokine & Growth Factor Reviews, 24, 4, 2013, pp. 319-333. (Year: 2013).*
Haanen et al. Immune Checkpoint Inhibitors. Prog Tumor Res. 2015; 42: Abstract (Year: 2015).*
Meyer et al., "Pseudotyping exosomes for enhanced protein delivery in mammalian cells". International Journal of Nanomedicine, Apr. 18, 2017, vol. 2017, pp. 3153-3170 (Year: 2017).*
Sun et al., "Advances in anticancer protein delivery using micro-/nanoparticles". Particle & Particle Systems Characterization, 2014, vol. 31, pp. 1204-1222 (Year: 2014).*
Mangeot et al., "Vesicular stomatitis virus (VSV-G) promotes the cell-release of a sedimentable agent capable of pseudotransduction," Mol Ther. vol. 19, No. 9, pp. 1656-1666 (Sep. 2011) (Published online Jul. 2011).
Duong et al., "Engineering exosomes towards therapeutics," Santa Clara University, Poster (2016).
Ha et al., "Exosomes as therapeutic drug carriers and delivery vehicles across biological membranes: current perspectives and future challenges," Acta Pharmaceutica Sinica B, vol. 6, Issue 4, pp. 287-296 (Jul. 2016).
Haney et al., "Exosomes as drug delivery vehicles for Parkinson's disease therapy," Journal of Controlled Release, vol. 207, pp. 18-30 (Jun. 2015).
Johnsen et al., "A comprehensive overview of exosomes as drug delivery vehicles—Endogenous nanocarriers for targeted cancer therapy," Biochimica et Biophysica Acta 1846 , pp. 75-87 (2014) (Available online Apr. 2014).
Meyer et al., Pseudotyping exosomes for enhanced protein delivery in mammalian cells, International Journal of Nanomedicine, vol. 12, pp. 3153-3170 (2017).
Roche et al., "Structure of the Prefusion Form of the Vesicular Stomatitis Virus Glycoprotein G," Science, vol. 315, Issue 5813, pp. 843-848 (Feb. 2007).
Roche et al., "Crystal structure of the low-pH form of the vesicular stomatitis virus glycoprotein G," Science, 313 (5784) pp. 187-191 (Jul. 2006).
Shtam et al., "Exosomes are natural carriers of exogenous siRNA to human cells in vitro," Cell Commun Signal, vol. 11, p. 88 (Nov. 2013).
Sun et al., "Advances in Anticancer Protein Delivery using Micro-/Nanoparticles," Particle & Particle Systems Characterization, vol. 31, pp. 1-19 (2014).
Tian et al., "A doxorubicin delivery platform using engineered natural membrane vesicle exosomes for targeted tumor therapy," Biomaterials, 35(7):2383-90 (Feb. 2014).
Yang et al., "Exosome delivered anticancer drugs across the blood-brain barrier for brain cancer therapy in Danio rerio," Phar Res., vol. 32, No. 6, pp. 2003-2014 (Jun. 2015).
Zhu et al., "Systemic Delivery of Fusogenic Membrane Glycoprotein-expressing Neural Stem Cells to Selectively Kill Tumor Cells," Molecular Therapy, vol. 21 No. 8, pp. 1621-1627, Aug. 2013 (Published online Jun. 2013).

(Continued)

*Primary Examiner* — Allison M Fox
*Assistant Examiner* — Hanan Isam Abuzeineh
(74) *Attorney, Agent, or Firm* — James S. Keddie; Bozicevic, Field & Francis LLP

(57) ABSTRACT

The present invention relates to a recombinant plasma membrane-based vesicle, and more specifically to a recombinant plasma membrane-based vesicle comprising a VSV-G mutated protein in which histidine, the $162^{nd}$ amino acid, has been substituted with arginine, and a pharmaceutical composition for treating cancer comprising the recombinant plasma membrane-based vesicle.

15 Claims, 20 Drawing Sheets
Specification includes a Sequence Listing.

(56) References Cited

OTHER PUBLICATIONS

Kim et al., "Xenogenization of tumor cells by fusogenic exosomes in tumor microenvironment ignites and propagates antitumor immunity", Science Advances, Jul. 1, 2020, 6: eaaz2083, 13 pages.
Jang et al., "Bioinspired Exosome-Mimetic Nanovesicles for Targeted Delivery of Chemotherapeutics to Malignant Tumors", ACS Nano, 2013, 7(9): 7698-7710.
Beyer et al., Genbank Accession No. CAC47944.1; VSV-G protein. submitted Jan. 23, 2002.

* cited by examiner

[Construct]

FIG. 2b

```
                       SEQ ID NO: 7                    SEQ ID NO: 9     H
                              162
Original VSV-G sequence : C P T V H N S T T    AAATGCAGCAATTACATATGCCCACTGTCCATAACTCTACAACCTGGCATTCTGAC
Mutated VSV-G sequence : C P T V R N S T T    ||||||||||||||||||||||||||||||||||||||||||||||||||||||||
                       SEQ ID NO: 8            AAATGCAGCAATTACATATGCCCACTGTCCGCAACTCTACAACCTGGCATTCTGAC
                                                                       SEQ ID NO: 10    R
```

[Sequence]

FIG. 3

300g, 10min
↓ SPNT 2000g, 10min
↓ SPNT 10,000g, 30min
↓ SPNT
↓ 0.2 μM filter

2729g,
Concentration with Amicon ultra centrifugal filter
↓

150,000g, 3 hr
↓ Pellet

Exosomes

[Western blot]

[TEM]

[DLS]

FIG. 6b
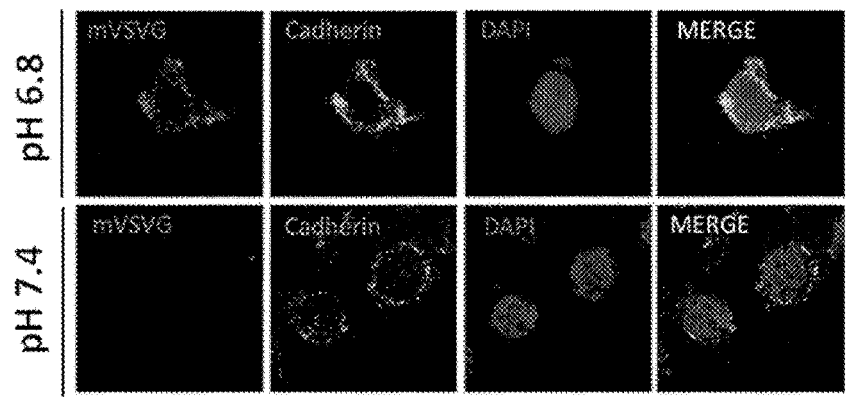
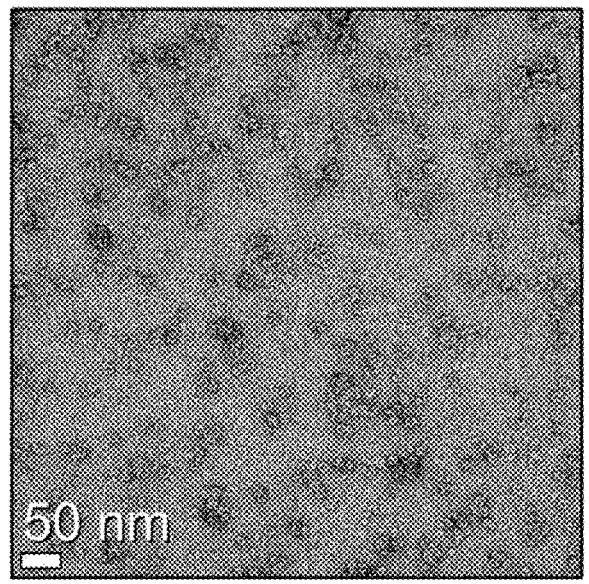
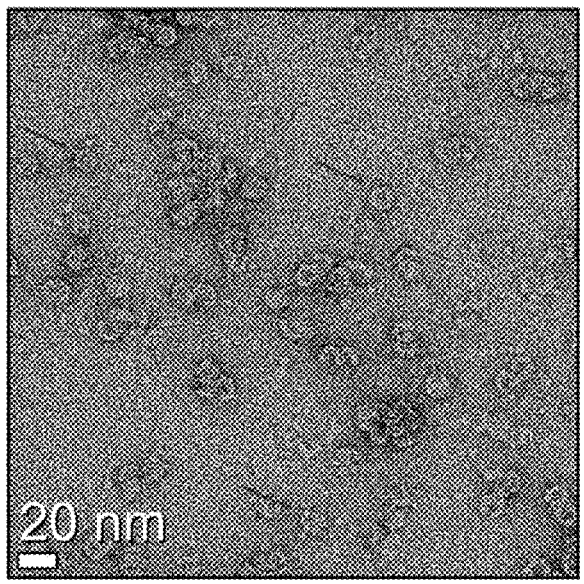

SEQUENCE LISTING

```
<160> NUMBER OF SEQ ID NOS: 10

<210> SEQ ID NO 1
<211> LENGTH: 511
<212> TYPE: PRT
<213> ORGANISM: Artificial Sequence
<220> FEATURE:
<223> OTHER INFORMATION: wild type VSV-G protein

<400> SEQUENCE: 1

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95
```

```
Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
        450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```

<210> SEQ ID NO 2
<211> LENGTH: 1536
<212> TYPE: DNA
<213> ORGANISM: Artificial Sequence
<220> FEATURE:
<223> OTHER INFORMATION: polynucleotide encoding wild type VSV-G protein

<400> SEQUENCE: 2

| | | | | | |
|---|---|---|---|---|---|
| atgaagtgcc | ttttgtactt | agcctttta | ttcattgggg | tgaattgcaa | gttcaccata | 60 |
| gttttttccac | acaaccaaaa | aggaaactgg | aaaaatgttc | cttctaatta | ccattattgc | 120 |
| ccgtcaagct | cagatttaaa | ttggcataat | gacttaatag | gcacagcctt | acaagtcaaa | 180 |
| atgcccaaga | gtcacaaggc | tattcaagca | gacggttgga | tgtgtcatgc | ttccaaatgg | 240 |
| gtcactactt | tgtgatttccg | ctggtatgga | ccgaagtata | aacacattc | catccgatcc | 300 |
| ttcactccat | ctgtagaaca | atgcaaggaa | agcattgaac | aaacgaaaca | aggaacttgg | 360 |
| ctgaatccag | gcttccctcc | tcaaagttgt | ggatatgcaa | ctgtgacgga | tgccgaagca | 420 |
| gtgattgtcc | aggtgactcc | tcaccatgtg | ctggttgatg | aatacacagg | agaatgggtt | 480 |
| gattcacagt | tcatcaacgg | aaaatgcagc | aattacatat | gccccactgt | ccataactct | 540 |
| acaacctggc | attctgacta | taaggtcaaa | gggctatgtg | attctaacct | catttccatg | 600 |
| gacatcacct | tcttctcaga | ggacggagag | ctatcatccc | tgggaaagga | gggcacaggg | 660 |
| ttcagaagta | actactttgc | ttatgaaact | ggaggcaagg | cctgcaaaat | gcaatactgc | 720 |
| aagcattggg | gagtcagact | cccatcaggt | gtctggttcg | agatggctga | taaggatctc | 780 |
| tttgctgcag | ccagattccc | tgaatgccca | gaagggtcaa | gtatctctgc | tccatctcag | 840 |
| acctcagtgg | atgtaagtct | aattcaggac | gttgagagga | tcttggatta | ttccctctgc | 900 |
| caagaaacct | ggagcaaaat | cagagcgggt | cttccaatct | ctccagtgga | tctcagctat | 960 |
| cttgctccta | aaaacccagg | aaccggtcct | gctttcacca | taatcaatgg | taccctaaaa | 1020 |
| tactttgaga | ccagatacat | cagagtcgat | attgctgctc | caatcctctc | aagaatggtc | 1080 |
| ggaatgatca | gtggaactac | cacagaaagg | gaactgtggg | atgactgggc | accatatgaa | 1140 |
| gacgtggaaa | ttggacccaa | tggagttctg | aggaccagtt | caggatataa | gtttcctta | 1200 |
| tacatgattg | gacatggtat | gttggactcc | gatcttcatc | ttagctcaaa | ggctcaggtg | 1260 |
| ttcgaacatc | ctcacattca | agacgctgct | tcgcaacttc | ctgatgatga | agtttatttt | 1320 |
| tttggtgata | ctgggctatc | caaaaatcca | atcgagcttg | tagaaggttg | gttcagtagt | 1380 |
| tggaaaagct | ctattgcctc | ttttttcttt | atcatagggt | taatcattgg | actattcttg | 1440 |
| gttctccgag | ttggtatcca | tctttgcatt | aaattaaagc | acaccaagaa | aagacagatt | 1500 |
| tatacagaca | tagagatgaa | ccgacttgga | aagtaa | | | 1536 |

<210> SEQ ID NO 3
<211> LENGTH: 33
<212> TYPE: DNA
<213> ORGANISM: Artificial Sequence
<220> FEATURE:
<223> OTHER INFORMATION: forward primer

<400> SEQUENCE: 3
atatgcccca ctgtccgcaa ctctacaacc tgg         33

<210> SEQ ID NO 4
<211> LENGTH: 33
<212> TYPE: DNA
<213> ORGANISM: Artificial Sequence

```
<220> FEATURE:
<223> OTHER INFORMATION: reverse primer

<400> SEQUENCE: 4
tatacggggt gacaggcgtt gagatgttgg acc                                    33

<210> SEQ ID NO 5
<211> LENGTH: 511
<212> TYPE: PRT
<213> ORGANISM: Artificial Sequence
<220> FEATURE:
<223> OTHER INFORMATION: VSV-G H162R variant

<400> SEQUENCE: 5
```

| Met | Lys | Cys | Leu | Leu | Tyr | Leu | Ala | Phe | Leu | Phe | Ile | Gly | Val | Asn | Cys |
|---|---|---|---|---|---|---|---|---|---|---|---|---|---|---|---|
| 1 | | | | 5 | | | | | 10 | | | | | 15 | |

| Lys | Phe | Thr | Ile | Val | Phe | Pro | His | Asn | Gln | Lys | Gly | Asn | Trp | Lys | Asn |
|---|---|---|---|---|---|---|---|---|---|---|---|---|---|---|---|
| | | | 20 | | | | | 25 | | | | | 30 | | |

| Val | Pro | Ser | Asn | Tyr | His | Tyr | Cys | Pro | Ser | Ser | Ser | Asp | Leu | Asn | Trp |
|---|---|---|---|---|---|---|---|---|---|---|---|---|---|---|---|
| | | 35 | | | | | 40 | | | | | 45 | | | |

| His | Asn | Asp | Leu | Ile | Gly | Thr | Ala | Leu | Gln | Val | Lys | Met | Pro | Lys | Ser |
|---|---|---|---|---|---|---|---|---|---|---|---|---|---|---|---|
| 50 | | | | | 55 | | | | | 60 | | | | | |

| His | Lys | Ala | Ile | Gln | Ala | Asp | Gly | Trp | Met | Cys | His | Ala | Ser | Lys | Trp |
|---|---|---|---|---|---|---|---|---|---|---|---|---|---|---|---|
| 65 | | | | | 70 | | | | | 75 | | | | | 80 |

| Val | Thr | Thr | Cys | Asp | Phe | Arg | Trp | Tyr | Gly | Pro | Lys | Tyr | Ile | Thr | His |
|---|---|---|---|---|---|---|---|---|---|---|---|---|---|---|---|
| | | | | 85 | | | | | 90 | | | | | 95 | |

| Ser | Ile | Arg | Ser | Phe | Thr | Pro | Ser | Val | Glu | Gln | Cys | Lys | Glu | Ser | Ile |
|---|---|---|---|---|---|---|---|---|---|---|---|---|---|---|---|
| | | | 100 | | | | | 105 | | | | | 110 | | |

| Glu | Gln | Thr | Lys | Gln | Gly | Thr | Trp | Leu | Asn | Pro | Gly | Phe | Pro | Pro | Gln |
|---|---|---|---|---|---|---|---|---|---|---|---|---|---|---|---|
| | | 115 | | | | | 120 | | | | | 125 | | | |

| Ser | Cys | Gly | Tyr | Ala | Thr | Val | Thr | Asp | Ala | Glu | Ala | Val | Ile | Val | Gln |
|---|---|---|---|---|---|---|---|---|---|---|---|---|---|---|---|
| | 130 | | | | | 135 | | | | | 140 | | | | |

| Val | Thr | Pro | His | His | Val | Leu | Val | Asp | Glu | Tyr | Thr | Gly | Glu | Trp | Val |
|---|---|---|---|---|---|---|---|---|---|---|---|---|---|---|---|
| 145 | | | | | 150 | | | | | 155 | | | | | 160 |

| Asp | Ser | Gln | Phe | Ile | Asn | Gly | Lys | Cys | Ser | Asn | Tyr | Ile | Cys | Pro | Thr |
|---|---|---|---|---|---|---|---|---|---|---|---|---|---|---|---|
| | | | | 165 | | | | | 170 | | | | | 175 | |

| Val | Arg | Asn | Ser | Thr | Thr | Trp | His | Ser | Asp | Tyr | Lys | Val | Lys | Gly | Leu |
|---|---|---|---|---|---|---|---|---|---|---|---|---|---|---|---|
| | | | 180 | | | | | 185 | | | | | 190 | | |

| Cys | Asp | Ser | Asn | Leu | Ile | Ser | Met | Asp | Ile | Thr | Phe | Phe | Ser | Glu | Asp |
|---|---|---|---|---|---|---|---|---|---|---|---|---|---|---|---|
| | | 195 | | | | | 200 | | | | | 205 | | | |

| Gly | Glu | Leu | Ser | Ser | Leu | Gly | Lys | Glu | Gly | Thr | Gly | Phe | Arg | Ser | Asn |
|---|---|---|---|---|---|---|---|---|---|---|---|---|---|---|---|
| | 210 | | | | | 215 | | | | | 220 | | | | |

| Tyr | Phe | Ala | Tyr | Glu | Thr | Gly | Gly | Lys | Ala | Cys | Lys | Met | Gln | Tyr | Cys |
|---|---|---|---|---|---|---|---|---|---|---|---|---|---|---|---|
| 225 | | | | | 230 | | | | | 235 | | | | | 240 |

| Lys | His | Trp | Gly | Val | Arg | Leu | Pro | Ser | Gly | Val | Trp | Phe | Glu | Met | Ala |
|---|---|---|---|---|---|---|---|---|---|---|---|---|---|---|---|
| | | | | 245 | | | | | 250 | | | | | 255 | |

| Asp | Lys | Asp | Leu | Phe | Ala | Ala | Ala | Arg | Phe | Pro | Glu | Cys | Pro | Glu | Gly |
|---|---|---|---|---|---|---|---|---|---|---|---|---|---|---|---|
| | | | 260 | | | | | 265 | | | | | 270 | | |

| Ser | Ser | Ile | Ser | Ala | Pro | Ser | Gln | Thr | Ser | Val | Asp | Val | Ser | Leu | Ile |
|---|---|---|---|---|---|---|---|---|---|---|---|---|---|---|---|
| | | 275 | | | | | 280 | | | | | 285 | | | |

| Gln | Asp | Val | Glu | Arg | Ile | Leu | Asp | Tyr | Ser | Leu | Cys | Gln | Glu | Thr | Trp |
|---|---|---|---|---|---|---|---|---|---|---|---|---|---|---|---|
| | 290 | | | | | 295 | | | | | 300 | | | | |

| Ser | Lys | Ile | Arg | Ala | Gly | Leu | Pro | Ile | Ser | Pro | Val | Asp | Leu | Ser | Tyr |
|---|---|---|---|---|---|---|---|---|---|---|---|---|---|---|---|
| 305 | | | | | 310 | | | | | 315 | | | | | 320 |

| Leu | Ala | Pro | Lys | Asn | Pro | Gly | Thr | Gly | Pro | Ala | Phe | Thr | Ile | Ile | Asn |
|---|---|---|---|---|---|---|---|---|---|---|---|---|---|---|---|
| | | | | 325 | | | | | 330 | | | | | 335 | |

```
Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
            405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
            435                 440                 445

Asn Pro Ile Glu Leu Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
            485                 490                 495

Lys Arg Gln Ile Tyr Thr Asp Ile Glu Met Asn Arg Leu Gly Lys
            500                 505                 510
```

<210> SEQ ID NO 6
<211> LENGTH: 1536
<212> TYPE: DNA
<213> ORGANISM: Artificial Sequence
<220> FEATURE:
<223> OTHER INFORMATION: polynucleotide encoding VSV-G H162R variant

<400> SEQUENCE: 6

```
atgaagtgcc ttttgtactt agcctttta ttcattgggg tgaattgcaa gttcaccata      60
gttttccac acaaccaaaa aggaaactgg aaaaatgttc cttctaatta ccattattgc     120
ccgtcaagct cagatttaaa ttggcataat gacttaatag cacagcctt acaagtcaaa     180
atgcccaaga gtcacaaggc tattcaagca gacggttgga tgtgtcatgc ttccaaatgg     240
gtcactactt gtgatttccg ctggtatgga ccgaagtata acacattc atccgatcc      300
ttcactccat ctgtagaaca atgcaaggaa agcattgaac aaacgaaaca ggaacttgg     360
ctgaatccag cttccctcc tcaaagttgt ggatatgcaa ctgtgacgga tgccgaagca     420
gtgattgtcc aggtgactcc tcaccatgtg ctggttgatg aatacacagg agaatgggtt    480
gattcacagt tcatcaacgg aaaatgcagc aattacatat gccccactgt ccgcaactct    540
acaacctggc attctgacta taaggtcaaa gggctatgtg attctaacct catttccatg    600
gacatcacct tcttctcaga ggacggagag ctatcatccc tgggaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct aattcaggac gttgagagga tcttggatta ttccctctgc    900
caagaaacct ggagcaaaat cagagcgggt cttccaatct ctccagtgga tctcagctat    960
cttgctccta aaaacccagg aaccggtcct gctttcacca taatcaatgg taccctaaaa    1020
tactttgaga ccagatacat cagagtcgat attgctgctc aatcctctc aagaatggtc    1080
```

```
ggaatgatca gtggaactac cacagaaagg gaactgtggg atgactgggc accatatgaa    1140
gacgtggaaa ttggacccaa tggagttctg aggaccagtt caggatataa gtttccttta    1200
tacatgattg gacatggtat gttggactcc gatcttcatc ttagctcaaa ggctcaggtg    1260
ttcgaacatc ctcacattca agacgctgct tcgcaacttc ctgatgatga gagtttattt    1320
tttggtgata ctgggctatc caaaaatcca atcgagcttg tagaaggttg gttcagtagt    1380
tggaaaagct ctattgcctc ttttttcttt atcataggg taatcattgg actattcttg    1440
gttctccgag ttggtatcca tctttgcatt aaattaaagc acaccaagaa aagacagatt    1500
tatacagaca tagagatgaa ccgacttgga aagtaa                              1536

<210> SEQ ID NO 7
<211> LENGTH: 9
<212> TYPE: PRT
<213> ORGANISM: Artificial Sequence
<220> FEATURE:
<223> OTHER INFORMATION: wildtype VSV-G histidine_162 flank region

<400> SEQUENCE: 7

Cys Pro Thr Val His Asn Ser Thr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: mutant VSV-G arginine_162 flank region

<400> SEQUENCE: 8

Cys Pro Thr Val Arg Asn Ser Thr Thr
1               5

<210> SEQ ID NO 9
<211> LENGTH: 58
<212> TYPE: DNA
<213> ORGANISM: Artificial Sequence
<220> FEATURE:
<223> OTHER INFORMATION: polynucleotide encoding wildtype VSV-G
      histidine_162 flank region

<400> SEQUENCE: 9
aaaatgcagc aattacatat gccccactgt ccataactct acaacctggc attctgac        58

<210> SEQ ID NO 10
<211> LENGTH: 58
<212> TYPE: DNA
<213> ORGANISM: Artificial Sequence
<220> FEATURE:
<223> OTHER INFORMATION: polynucleotide encoding mutant VSV-G
      arginine_162 flank region

<400> SEQUENCE: 10
aaaatgcagc aattacatat gccccactgt ccgcaactct acaacctggc attctgac        58
```

RECOMBINANT PLASMA MEMBRANE-BASED VESICLE, FOR TREATING CANCER

CROSS-REFERENCE TO RELATED APPLICATIONS

The present application is the U.S. National Stage of International Application No. PCT/KR2018/011504, filed Sep. 28, 2018, and claims priority to Korean Patent Application No. 10-2017-0126202 filed Sep. 28, 2017.

SEQUENCE LISTING

The instant application contains a Sequence Listing which has been submitted electronically in ASCII format and is hereby incorporated by reference in its entirety. Said ASCII copy, created on Nov. 17, 2020, is named 122257-0112_201117_corrected_ST25.txt and is 14,844 bytes in size.

TECHNICAL FIELD

The present invention relates to a novel recombinant plasma membrane-based vesicle, and more specifically, to a novel recombinant plasma membrane-based vesicle for treating cancer.

BACKGROUND ART

Cancer refers to a group of diseases associated with abnormal cell growth with a potential for invasion and metastasis to other parts of the body. As of 2015, it is known that there are more than 90 million cancer patients worldwide, with about 14 million new cancer patients occurring every year. Cancer accounts for 15.7% of causes of human deaths. The most frequently occurring cancers are lung cancer, prostate cancer, colon cancer, and stomach cancer in men, and breast cancer, colon cancer, lung cancer, and uterine cervical cancer in women.

For cancer treatment, various therapeutic approaches are attempted, including chemotherapy using various anticancer agents, radiation therapy by irradiation, antibody therapy targeting particular in vivo molecules associated with cancer, etc. However, anticancer agents used in chemotherapy or irradiation have serious side effects because these treatments also affect normal cells and often result in treatment failure or recurrence because cancer cells can acquire resistance to anticancer agents.

Recently, the anti-cancer immunotherapy using the immune system of our body has been showing a surprising effect in clinical treatment. However, due to the complexity of cancer, the anti-cancer immunotherapy has a limitation in that the therapy is only effective in less than about 30% of cancer patients. This is because cancer cells are recognized as "self" by our body's immune cells, and therefore, it is important for cancer cells to be recognized as "non-self" by immune cells, so that the phagocytosis of cancer cells can be induced thereby inducing an amplified immune response.

Exosomes are cell-derived vesicles present in all biological liquids, including blood, urine, and culture media of cell cultures, also called extracellular vesicles or microvesicles. Exosomes are known to have a size between 30 nm and 100 nm, and are secreted from cells when the multivesicular body fuses with a cell membrane, secreted directly through a cell membrane, or are budding directly from a cell membrane. Exosomes are known to play an important role in various processes such as coagulation, intercellular signaling, and metabolic waste management. Exosomes have important advantages as drug carriers compared to liposomes or polymer-type nanoparticles in that exosomes have compositions similar to those of the cells themselves of the human body and in that exosomes are non-immunogenic (Ha et al., *Acta Pharm. Sin. B.* 6(4): 287-296, 2016). In this regard, various attempts have been made using exosomes so that anticancer drugs (e.g., doxorubicin) are delivered to a tumor tissue (Tian et al., *Biomaterials.* 35:2383-2390, 2014); paclitaxel and doxorubicin pass through the blood brain barrier and are delivered to the brain (Yang et al., *Pharm. Res.* 32:2003-2014, 2015); for treatment of Parkinson's disease, catalase passes through the blood brain barrier and is delivered to the brain (Haney et al., *J. Control Release.* 207: 18-30, 2015); or for treatment of cancer, siRNAs specific to certain genes are delivered (Shtam et al., *Cell Commun. Signal.* 11: 88, 2013), etc.

An extracellular vesicle refers to a structure in the form of a particle, in which various biomolecules (e.g., proteins, nucleic acid molecules (e.g., RNA), lipids of various functions, etc.) released or secreted from cells into an extracellular environment are enclosed in a cell membrane of a lipid bilayer identical to the cell membrane of the cell from which the various biomolecules are derived. The extracellular vesicle refers to a plasma membrane-based vesicle having an average diameter of 100 nm to 1 μm, which is larger than that of an exosome normally having a size of 30 nm to 100 nm.

A cell-derived nanovesicle, which is a nano-sized vesicle surrounded by a plasma membrane which is a nano-sized cell membrane component formed by artificial methods (e.g., an extrusion process where cells are passed through microfluidic channels, a multi-stage filtration process, etc.), refers to a plasma membrane-based vesicle distinguished from an exosome or extracellular vesicle secreted by a cell and formed naturally.

Meanwhile, vesicular stomatitis virus glycoprotein (VSV-G) is the only virus glycoprotein present in the virion membrane of vesicular stomatitis virus and acts as a protein for adhesion and fusion of the virus into a target cell. The VSV-G protein is a transmembrane protein including two N-linked glycans, which can initiate a membrane fusion event in a low-pH-dependent manner when no other virus protein is present. Since VSV-G proteins can form a complex with a nucleic acid molecule such as DNA, VSV-G proteins have been used as a carrier for direct gene transfer, or have been used effectively in gene therapy by producing more stable and high-titer pseudotyped murine leukemia virus (MLV)-based retrovirus and lentivirus-based vectors. Recently, however, it has been suggested that VSV-G proteins be available for use to deliver various proteins, in addition to genes, to heterologous cells (Mangeot et al., *Mol. Ther.* 19(9): 1656-1666, 2011).

As a result of the research on the structures and functions of the VSV-G proteins, it was previously confirmed that histidine, which is the $60^{th}$, the $162^{nd}$, and the $407^{th}$ amino acid residues based on the mature protein from which the signal sequence was removed, forms a cluster and acts as a pH sensor (Roche et al., *Science,* 313: 187-191, 2006; Roche et al., *Science,* 315: 843-848, 2007), and recently, it was reported that when the $162^{nd}$ amino acid residue, histidine, among the above histidine residues is mutated into arginine (H162R), it induces a membrane fusion at pH 6.8, which is a physiological pH surrounding cancer cells, and promotes the death of cancer cells upon administration of neural stem cells expressing the VSV-G mutant (H162R) (Zhu et al., *Mol. Ther.* 21 (8) : 1492-1497, 2013).

However, the method disclosed in the related art is a technology difficult to apply to the actual clinical environment in that the supply of neural stem cells is difficult, and that the cancer cell killing effect is not very significant.

DISCLOSURE OF THE INVENTION

Technical Problem

The objects of the present invention are to solve various problems including the above problems, and an object of the present invention is to provide a recombinant plasma membrane-based vesicle for safe cancer treatment which does not operate under conditions outside the cancer microenvironment while efficiently killing cancer cells on their own without an anticancer agent. In particular, the object of the present invention is to provide a recombinant plasma membrane-based vesicle which enables "xenogenization" so that immune cells can recognize cancer cells as an "enemy". However, these objects are illustrative, and the scope of the present invention is not limited thereby.

Technical Solution

According to an aspect of the invention, there is provided a recombinant plasma membrane-based vesicle, wherein a VSV-G mutant protein in which the $162^{nd}$ amino acid, histidine, is substituted with arginine is introduced into the membrane.

According to another aspect of the invention, there is provided a pharmaceutical composition for treating cancer containing the recombinant plasma membrane-based vesicle as an active ingredient.

Moreover, according to still another aspect of the invention, there is provided a pharmaceutical composition for treating cancer containing a recombinant plasma membrane-based vesicle, in which a virus-derived fusogenic membrane protein is introduced into the membrane, as an active ingredient.

Moreover, according to still another aspect of the invention, there is provided a recombinant plasma membrane-based vesicle, wherein a VSV-G mutated protein in which the $162^{nd}$ amino acid, histidine, is substituted with arginine is introduced into the membrane; or the use of a recombinant plasma membrane-based vesicle, in which a virus-derived fusogenic membrane protein is introduced into the membrane, for the preparation of a cancer therapeutic agent.

According to still another aspect of the invention, there is provided a method for treating cancer in a subject with cancer, which includes administering the recombinant plasma membrane-based vesicle or one or more pharmaceutical compositions among those described above to the subject with cancer.

Advantageous Effects

According to an embodiment of the present invention constituted as described above, the present invention can effectively treat cancer without resorting to a complex mechanism such as gene transfer.

BRIEF DESCRIPTION OF THE DRAWINGS

FIG. 2b shows amino acid sequences illustrating the wild-type VSV-G protein and the mutation at position 162 of a mutated VSV-G protein for producing a recombinant exosome according to an embodiment of the present invention, and the nucleic acid sequences of the polynucleotides encoding the same.

FIG. 3 is a process chart illustrating a process for producing a recombinant exosome including mVSV-G according to an embodiment of the present invention.

FIG. 6b shows a series of fluorescence microscopic images of the 4T1-Luc cells after staining the 4T1-Luc cells using an anti-VSV-G antibody and an anti-Cadherin antibody (green), when 4T1-Luc cells were treated with the mVSVG-Exo according to an embodiment of the present invention, as to whether there was a membrane fusion with cancer cells according to pH change.

FIG. 7b shows a series of graphs illustrating the results of quantitative measurements of the results of FIG. 7a.

FIG. 10b is a graph illustrating the measurement results of the weight of cancer tissues extracted by sacrificing experimental animals 16 days after cancer cell injection in FIG. 10a.

FIG. 11b is a graph illustrating the measurement results of the weight of cancer tissues extracted by sacrificing experimental animals 16 days after cancer cell injection in FIG. 11a.

FIG. 15a shows the experimental results according to a low dose (two times of administration: 100 μg each); FIG. 15b shows the results of the administration according to a high dose (four times of administration: 100 μg each) using the same model.

MODE FOR CARRYING OUT THE INVENTION

Definition of Terms

Figure 1:
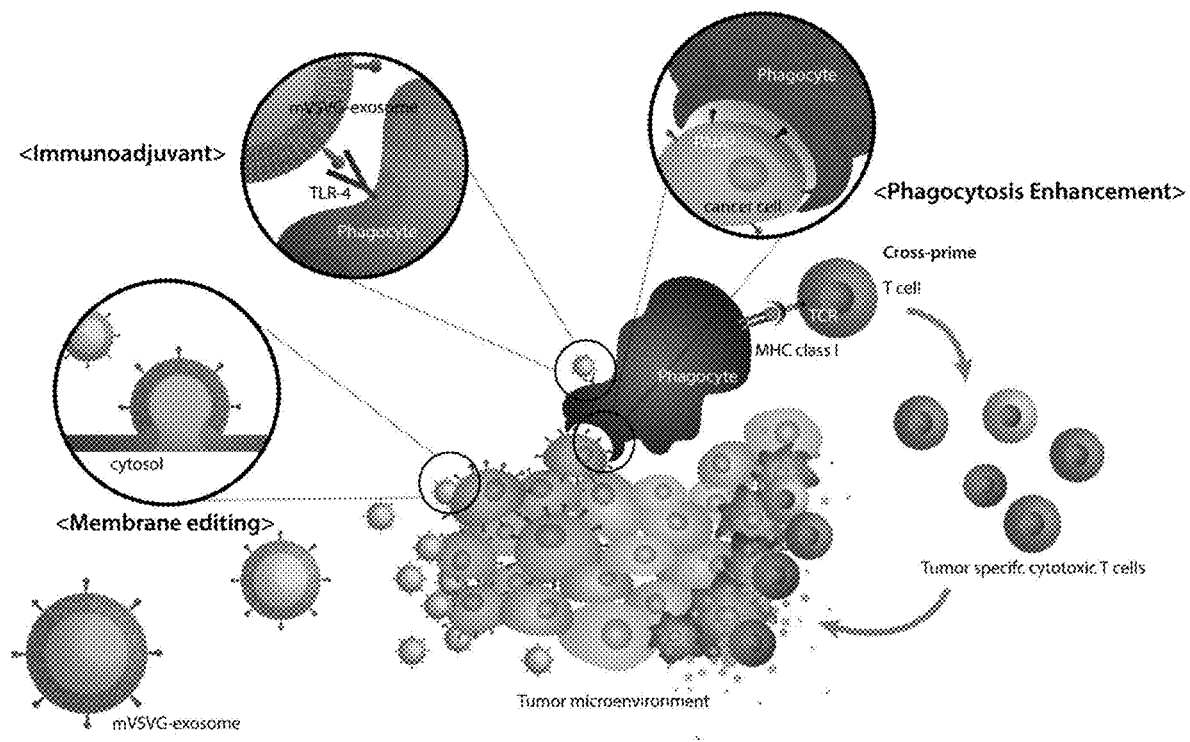
FIG. 1 is a schematic diagram schematically illustrating a mechanism of action of a recombinant exosome, which includes a mutant VSV-G H162R (hereinafter abbreviated as "mVSV-G") that induces anticancer immune effects in a cancer cell microenvironment (pH 6.8), according to an embodiment of the present invention.
Figure 2A:
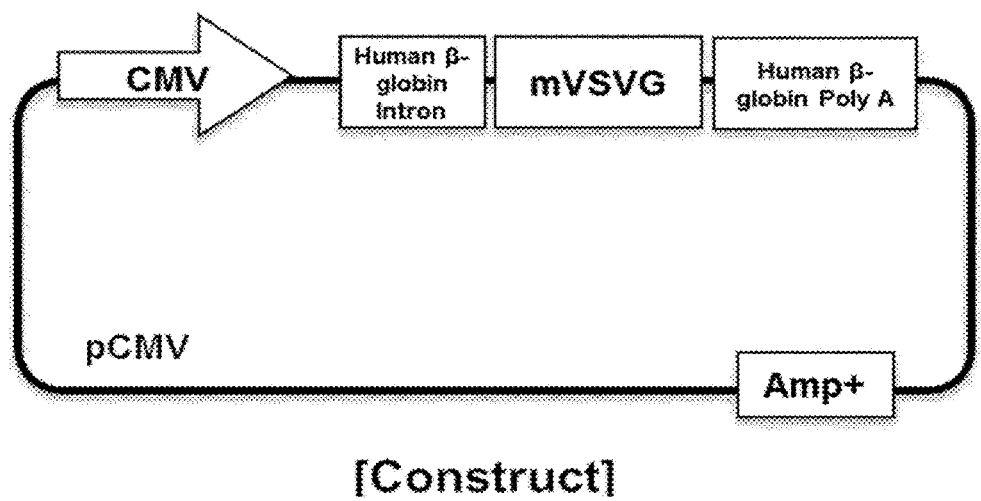
FIG. 2a is a plasmid map illustrating a schematic structure of the plasmid DNA for producing a recombinant exosome according to an embodiment of the present invention.

As used herein, the term "fusogenic membrane protein" refers to a virus-derived membrane protein which plays a key role in inducing the adhesion and membrane fusion of a virus to a host cell for the penetration of the virus into the host cell. A representative example is an envelope glycoprotein derived from the vesicular stomatitis virus (VSV-G).

As used herein, the term "an envelope glycoprotein derived from the vesicular stomatitis virus (VSV-G protein)" refers to the only virus glycoprotein present in the virion membrane of vesicular stomatitis virus and acts as a protein for adhesion and fusion to a heterologous cell of the virus. The VSV-G protein is a transmembrane protein including two N-linked glycans, and can initiate a membrane fusion in a low-pH-dependent manner in the absence of other viral proteins. The VSV-G protein can form a complex with a nucleic acid molecule such as DNA, and thus has been used as a carrier for direct gene transfer or has been used effectively in gene therapy by producing more stable and high-titer pseudotyped murine leukemia virus (MLV)-based retrovirus and lentivirus-based vectors. However, the availability of the VSV-G protein to be used for the delivery of various proteins, in addition to genes, to heterologous cells has recently been proposed (Mangeot et al., *Mol. Ther.* 19(9): 1656-1666, 2011).

As used herein, the term "plasma membrane-based vesicle" refers to a nano-sized vesicle surrounded by a cell membrane derived from a cell, and includes exosomes produced by secretion or budding from cells, cell-derived nanovesicles prepared by processing extracellular vesicles or cells by an artificial method (e.g., extrusion, etc.), etc.

As used herein, the term "exosome" refers to a cell-derived vesicle present in all biological liquids, including blood, urine, and culture media of cell cultures, and is also called an extracellular vesicle or a microvesicle. Exosomes are known to have a size between 30 nm and 100 nm, and are secreted from cells when the multivesicular body fuses with a cell membrane or secreted directly through a cell membrane. Exosomes are known to play an important role in various processes such as coagulation, intercellular signaling, and metabolic waste management.

As used herein, the term "recombinant exosome" refers to an artificially-produced exosome, which is obtained in such a manner that a transformed host cell is prepared by genetic engineering in which a gene encoding a heterologous protein is transduced into a host cell capable of producing exosomes, and the transformed host cell is cultured and the exosome is obtained from the culture liquid. The recombinant exosome includes a transduced heterologous protein either inside or on exosomal membrane.

As used herein, the term "extracellular vesicle" refers to a structure in the form of a particle, in which various biomolecules (e.g., proteins, nucleic acid molecules (e.g., RNA), lipids of various functions, etc.) released or secreted from cells into an extracellular environment are enclosed in a cell membrane of a lipid bilayer identical to the cell membrane of the cell from which the various biomolecules are derived. An extracellular vesicle refers to a plasma membrane-based vesicle having an average diameter of 100 nm to 1 μm, which is larger than that of an exosome normally having a size of 30 nm to 100 nm.

As used herein, the term "cell-derived nanovesicle", which is a nano-sized vesicle surrounded by a plasma membrane that is a nano-sized cell membrane component formed by artificial methods (e.g., an extrusion process where cells are passed through microfluidic channels, a multi-stage filtration process, etc.), refers to a plasma membrane-based vesicle distinguished from an exosome or extracellular vesicle secreted by a cell and formed naturally.

As used herein, the term "immunogenic cell death" refers to a kind of cell death caused by cell proliferation inhibitors (e.g., anthracyclines, oxaliplatin, and bortezomib) or by radiation therapy and photodynamic therapy. Unlike normal cell death, the immunogenic cell death, that is, the immunological cell death of cancer cells can induce an effective anticancer immune response via activation of dendritic cells and subsequent activation of a specific T cell response. The material which induces the immunogenic cell death is called an "immunogenic cell death inducer". The immunogenic cell death and the immunogenic cell death inducers are well summarized in Kroemer et al. (*Anna. Rev. Immunol.,* 31: 51-72, 2013). This document is incorporated herein by reference in its entirety.

As used herein, the term "anthracycline-type anticancer agent" refers to a cell-cycle nonspecific anticancer agent family used in cancer chemotherapy derived from *Streptomyces peucetius* var. *caesius*. The anthracycline-type anticancer agent is used to treat various cancers, including leukemia, lymphoma, breast cancer, stomach cancer, uterine cancer, ovarian cancer, bladder cancer, and lung cancer, and is one of the most effective anticancer agents among the chemotherapy anticancer agents that have been developed. The first found anthracycline-type anticancer agent was daunorubicin, immediately followed by doxorubicin, and subsequently followed by epirubicin, idarubicin, pixantrone, sabarubicin, valrubicin, etc., which are developed thereafter. Examples of the mechanism of action of anthracycline-type anticancer agents being proposed include: prevention of the replication of rapidly growing cancer cells by inhibiting DNA and RNA synthesis via intercalation between the bases of DNA/RNA strands; prevention of transcription and replication by inhibiting the relaxation of supercoiled DNA via suppression of the enzyme activity of topoisomerase II; induction of damage to DNA, proteins, and cell membranes through the formation of iron-mediated free oxygen radicals and DNA damage responses; induction of histone eviction from chromatin that deregulates epigenome and transcripts, etc. Recent study has reported that doxorubicin increases Th1 immune responses by activating CD4$^+$ cells (Park et al., *Int. Immunopharmacol.* 9(13-14): 1530-1539, 2009), and co-administration of dendritic cells with doxorubicin has been reported to show an anticancer activity by inducing immunogenic cell death of osteosarcoma (Kawano et al., *Oncol. Lett.* 11:2169-2175, 2016).

As used herein, the term "taxane-type anticancer agent (taxanoid anticancer agent or taxane anticancer drug)" refers to a diterpenoid taxane derivative derived from *Taxus* sp. plants, which is a mitotic inhibitor having a mechanism capable of promoting the assembly of microtubules in cells while inhibiting the disassembly of microtubules therein. Currently commercialized drugs include paclitaxel and docetaxel. Among them, paclitaxel is a taxane-type anticancer agent derived from the periderm of *Taxus brevifolia* and was approved as a therapeutic agent for refractory ovarian cancer by the US FDA in 1992, whereas docetaxel is a taxane-type anticancer agent derived from *Taxus baccata* and has a similar efficacy to paclitaxel, is used for treatment of breast cancer, non-cell lung cancer, lymphoma, bladder cancer, etc., and has a higher hydrophilicity than paclitaxel. Recently, taxane-type anticancer agents have also been shown to have a mechanism to promote immunogenic cell death of cancer cells by sensitizing these cancer cells to cytotoxic T lymphocytes.

As used herein, the term "immune checkpoint inhibitor" refers to a type of drug that blocks certain proteins produced by certain types of immune system cells (e.g., T lymphocytes) and some cancer cells, and these proteins suppress immune responses and prevent T lymphocytes from killing cancer cells. Therefore, blocking of these proteins can release the "braking system" of the immune system thereby allowing T lymphocytes to kill cancer cells better. Examples of the "immune checkpoint" well known thus far include PD-1/PD-L1, CTLA-4/B7-1/B7-2, etc. Examples of the PD-1 inhibitors include pembrolizumab (trade name: Keytruda), nivolumab (trade name: Opdivo), etc. Examples of the PD-L1 inhibitors, as a ligand of PD-1, include atezolizumab (trade name: Tecentriq), avelumab (trade name: Bavencio), etc. Meanwhile, ipilimumab (trade name: Yervoy) has been approved by the USFDA as a CTLA-4 inhibitor that inhibits the interaction of CTLA-4/B7-1/B7-2. For the past few years, these drugs have achieved a remarkable success, especially in patients with metastatic melanoma or Hodgkin lymphoma and have shown great potential in clinical trials with respect to different types of cancer patients.

DETAILED DESCRIPTION OF THE INVENTION

According to an aspect of the present invention, there is provided a recombinant plasma membrane-based vesicle, wherein a VSV-G mutated protein in which the $162^{nd}$ amino acid, histidine, is substituted with arginine is introduced into the membrane.

The recombinant plasma membrane-based vesicle may be an exosome, an extracellular vesicle, or a cell-derived nanovesicle.

The recombinant plasma membrane-based vesicle may be isolated/purified from a mammalian cell, preferably from a human cell, which is transformed into a gene construct including a polynucleotide encoding the VSV-G mutated protein and thus overexpresses the VSV-G mutated protein.

The recombinant plasma membrane-based vesicle may be obtained from a cell which is transformed to express the VSV-G mutated protein.

According to another aspect of the present invention, there is provided a VSV-G mutated protein in which the $162^{nd}$ amino acid, histidine, is substituted with arginine is introduced into the membrane, and one or two or more immunogenic cell death inducers are incorporated therein.

The incorporation of a drug into the recombinant plasma membrane-based vesicle can be achieved by culturing cells, which are genetically engineered to produce a recombinant plasma membrane-based vesicle, in a cell culture medium into which the drug is dissolved; or can be produced by reconstituting the recombinant plasma membrane-based vesicles via sonication treatment in a solvent in which the immunogenic cell death inducer is dissolved (Kim et al., *Nanomedicine,* 12(3): 655-664, 2016). Optionally, when the drug is supported on the plasma membrane-based vesicle, a method in which the isolated plasma membrane-based vesicle can be simply mixed with a drug in an appropriate solvent or medium and then mixed by stirring for an appropriate period of time (Sun et al., *Mol. Ther.* 18(9): 1606-1614, 2010), or hydrophilic drugs (e.g., nucleic acids) can be incorporated into the plasma membrane-based vesicle by electroporation.

The immunogenic cell death inducer may be an anthracycline-type anticancer agent, a taxane-type anticancer agent, an anti-EGFR antibody, a BK channel agonist, bortezomib, cardiac glycoside, a cyclophosphamide-type anticancer agent, a GADD34/PP1 inhibitor, LV-tSMAC, measles virus, bleomycin, mitoxantrone, or oxaliplatin. The cardiac glycoside may be used in combination with a non-immunogenic cell death inducer; the GADD34/PP1 inhibitor may be used in combination with mitomycin; the anthracycline-type anticancer agent may be daunorubicin, doxorubicin, epirubicin, idarubicin, pixantrone, sabarubicin, or valrubicin; the taxane-type anticancer agent may be paclitaxel or docetaxel; and the anti-EGFR antibody may be cetuximab.

According to still another aspect of the present invention, there is provided a pharmaceutical composition for treating cancer containing the recombinant plasma membrane-based vesicle as an active ingredient.

According to still another aspect of the present invention, there is provided a pharmaceutical composition for treating cancer containing a recombinant plasma membrane-based vesicle, wherein a virus-derived fusogenic membrane protein is introduced into the membrane, as an active ingredient.

In the above pharmaceutical composition, the virus-derived fusogenic membrane protein may be a vesicular stomatitis virus (VSV)-G protein, gibbon ape leukemia virus (GALV.fus), influenza virus hemagglutinin, F protein of respiratory syncytial virus, HIV virus gp120 or gp41, E protein of flavivirus, E1 protein of alphavirus, baculovirus gp64, hepatitis C virus gp31 or gp70, H protein or F protein of measles virus, or ebola virus gp1 or gp2; and the VSV-G protein may be a wild-type VSV-G protein or a pH-sensitive mutant VSV-G protein, in which the $162^{nd}$ amino acid, histidine, is substituted with arginine.

The above pharmaceutical composition may further contain one or two or more anticancer compounds.

The anticancer compound may be an immunogenic cell death inducer or an immune checkpoint inhibitor; the immunogenic cell death inducer may be an anthracycline-type anticancer agent, a taxane-type anticancer agent, an anti-EGFR antibody, a BK channel agonist, bortezomib, cardiac glycoside, a cyclophosphamide-type anticancer agent, a GADD34/PP1 inhibitor, LV-tSMAC, measles virus, bleomycin, mitoxantrone, or oxaliplatin. The cardiac glycoside may be used in combination with a non-immunogenic cell death inducer; the GADD34/PP1 inhibitor may be used in combination with mitomycin; the anthracycline-type anticancer agent may be daunorubicin, doxorubicin, epirubicin, idarubicin, pixantrone, sabarubicin, or valrubicin; the taxane-type anticancer agent may be paclitaxel or docetaxel; and the anti-EGFR antibody may be cetuximab. Meanwhile, the immune checkpoint inhibitor may be a PD-1/PD-L1 interaction inhibitor or a CTLA-4/B7-1/B7-2 interaction inhibitor; the PD-1/PD-L1 interaction inhibitor may be an antibody targeting PD-1 or PDL1, or a functional fragment of the antibody, or a single chain-based antibody analog; the CTLA-4/B7-1/B7-2 interaction inhibitor may be an antibody targeting CTLA-4, B7-1, or B7-2, or a functional fragment of the antibody, or a single chain-based antibody analog; the antibody targeting PD-1 or PDL1 may be pembrolizumab, nivolumab, atezolizumab, or avelumab; and the CTLA-4/B7-1/B7-2 interaction inhibitor may be ipilimumab. Meanwhile, the functional fragment of the antibody may be Fab, $F(ab')_2$, or Fab'; and the single chain-based antibody analog may be scFv, sdAb, diabody, monobody, variable lymphocyte receptor (VLR), nanobody, or llama heavy chain antibody fragment ($V_HH$).

Meanwhile, in the above composition, the anticancer compound may be enclosed inside the plasma membrane-based vesicle, may be simply mixed and formulated, may be packaged separately and mixed immediately before use, or may be administered simultaneously or at staggered time intervals. However, when the immune checkpoint inhibitor is an antibody, a functional fragment of an antibody, or a single chain-based antibody analog, the immune checkpoint inhibitor may be enclosed inside the exosome, but may be co-administered with a recombinant plasma membrane-based vesicle derived from the cells of the invention, or may be presented on the membrane surface of the recombinant plasma membrane-based vesicle to exert the functions. When the antibody, a functional fragment of the antibody, or a single chain-based antibody analog is presented on the membrane surface of the recombinant plasma membrane-based vesicle, the recombinant plasma membrane-based vesicle, in which an immune checkpoint inhibitor according to an embodiment of the present invention is presented on the membrane surface, can be prepared in such a manner that a gene encoding the recombinant plasma membrane-based vesicle is transduced into host cells and expressed to be presented on the membrane surface of the host cells using genetic recombination technology in the same way as the virus-derived fusogenic membrane protein used in the present invention, and then, nano-sized vesicles, which are secreted or budding from these host cells or prepared by artificially processing the cells, are obtained. In this case, the antibody, a functional fragment of the antibody, or a single chain-based antibody analog may be genetically recombined with a separate transmembrane domain or anchoring domain in order to be presented on the cell membrane surface. Optionally, it is also possible to use at first IgM or IgD (i.e., a non-secreting membrane-bound antibody), instead of genetic recombination to have the transmembrane domain or membrane-anchoring domain.

In the case of the composition, the recombinant plasma membrane-based vesicle and the immunogenic cell death inducer may be provided in the form of a pre-mixed composition, may be packaged separately, and mixed and administered immediately prior to use, or administered separately at regular time intervals.

The pharmaceutical composition of the present invention may contain a pharmaceutically acceptable carrier. The composition containing a pharmaceutically acceptable carrier may be in various oral or parenteral formulations, but is preferably in a parenteral formulation. In formulating the composition, diluents or excipients such as fillers, extenders, binders, wetting agents, disintegrates, surfactants, etc. are commonly used. Solid formulations for oral administration include tablets, pills, powders, granules, capsules, etc. and these solid preparations are prepared by mixing at least one excipient (e.g., starch, calcium carbonate, sucrose or lactose, gelatin, etc.) in one or more compounds. In addition to simple excipients, lubricants (e.g., magnesium stearate, talc, etc.) may also be used. Liquid formulations for oral administration include suspensions, liquid medicine for internal use, emulsions, syrups, etc. and various excipients (e.g., wetting agents, sweeteners, fragrances, preservatives, etc.) may be included, in addition to commonly used simple diluents (e.g., water and liquid paraffin). Formulations for parenteral administration include sterile aqueous solutions, non-aqueous solvents, suspensions, emulsions, lyophilized preparations, and suppositories. Propylene glycol, polyethylene glycol, vegetable oils (e.g., olive oil), and injectable esters (e.g., ethyl oleate), etc. may be used as non-aqueous solvents and suspensions. Witepsol, macrogol, tween 61, cacao butter, laurin butter, glycerogelatin, etc. may be used as a base for suppositories.

The pharmaceutical composition may have any one formulation selected from the group consisting of tablets, pills, powders, granules, capsules, suspensions, solutions, emulsions, syrups, sterile aqueous solutions, non-aqueous solvents, lyophilized preparations, and suppositories.

The pharmaceutical composition of the present invention may be administered orally or parenterally. When the pharmaceutical composition is administered parenterally, it is possible to administer the pharmaceutical composition via various routes (e.g., intravenous injection, intranasal inhalation, intramuscular administration, intraperitoneal administration, transdermal absorption, etc.).

The composition of the present invention is administered in a pharmaceutically effective amount.

As used herein, the term "pharmaceutically effective amount" refers to an amount sufficient to treat a disease at a reasonable benefit/risk ratio applicable to medical treatment. Effective dosage levels may depend upon factors including the subject's type, the severity of the disease, the subject's age, sex, drug activity, sensitivity to the drug, the time of administration, the route of administration and the rate of excretion, the duration of treatment, drugs used concurrently, and other factors well-known in the medical arts. The pharmaceutical composition of the present invention may be administered at a dose of 0.1 mg/kg to 1 g/kg, and more preferably at a dose of 1 mg/kg to 500 mg/kg. Meanwhile, the dose may be appropriately adjusted according to the age, sex, and conditions of the patient.

The pharmaceutical compositions of the present invention may be administered either as an individual therapeutic agent or in combination with other anticancer agents, and may be administered sequentially or simultaneously with conventional anticancer agents, and may be administered single or multiple doses. Considering all the above factors, it is important to administer the amount that can obtain the maximum effect in a minimal amount without side effects, and the amount may be easily determined by those skilled in the art.

In addition, according to still another aspect of the present invention, there is provided a recombinant plasma membrane-based vesicle, wherein a VSV-G mutated protein in which the $162^{nd}$ amino acid, histidine, is substituted with arginine is introduced into the membrane; or the use of a recombinant plasma membrane-based vesicle, in which a virus-derived fusogenic membrane protein is introduced into the membrane, for the preparation of a cancer therapeutic agent.

According to still another aspect of the present invention, there is provided a method for treating cancer in a subject with cancer, which includes administering the recombinant plasma membrane-based vesicle or one or more pharmaceutical compositions among those described above to the subject with cancer.

In the above methods for treating cancer, the subject may be a human or a non-human mammal.

The inventors have prepared a recombinant exosome which presents the VGV-G H162R mutated protein on the surface (see FIGS. 2a to 5b) under the hypothesis that when a mutant (H162R) of a VSV-G protein (i.e., a fusogenic membrane protein) inducing fusion at low pH is introduced on the surface of an exosome and treated on cancer cells, a membrane fusion is not induced under normal physiological conditions (pH 7.4), but a membrane fusion is induced under conditions similar to the microenvironment of cancer tissues (pH 6.8), and since such a membrane fusion will allow the death of cancer cells and the VSV-G H162R mutated protein itself is a pathogen associated molecular pattern (PAMP), phagocytosis of phagocytes and cross-prime ability of dendritic cells will be enhanced (see FIG. 1). In fact, the recombinant exosome prepared as described above selectively induced a membrane fusion of cancer cells at pH 6.8 under in vitro conditions (see FIGS. 6a to 7b), but it was confirmed that the recombinant exosome did not induce death of cancer cells itself (see FIG. 7C). In addition, the recombinant exosome (mVSVG-Exo) according to an embodiment of the present invention promoted the phagocytosis of various cancer cells (4T1-Luc, EL4-Ova, and CT26.CL25) by macrophages and dendritic cells (see FIGS. 8a to 8c), and it was confirmed that this is a phenomenon that appears when the VSVG acts as a TLR4 agonist (see FIG. 9). When the recombinant exosome (mVSVG-Exo) was administered to a real tumor model animal, it was confirmed that the growth of the actual cancer cells was significantly inhibited without side effects (e.g., weight loss) (see FIGS. 10a to 11c), and it was confirmed by flow cytometry that the VSV-G protein was significantly expressed on the cell surface of tumor tissues extracted from the experimental animals (see FIG. 12). The above results suggest that the recombinant exosome of the present invention is a multifunctional anticancer agent that exhibits an anticancer activity through various mechanisms.

Figure 13A:
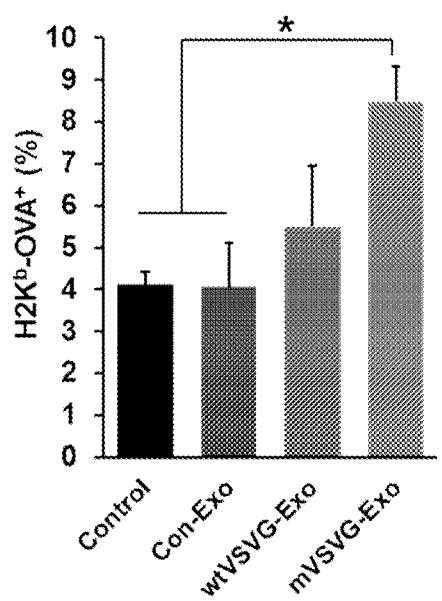
FIG. 13a is a graph illustrating the results of flow cytometry, in which a recombinant exosome including the mVSV-G (mVSVG-Exo) according to an embodiment of the present invention, a recombinant exosome including the wild-type VSV-G (wtVSVG-Exo), a control group exosome (Con-Exo), and PBS as the control group were administered into the cancer tissues of tumor model animals (EL4-Ova-injected C57BL/6 mice), and the extracted tumor-draining lymph nodes were converted into single cells, and subjected to flow cytometry analysis using an anti-CD11c antibody and an anti-H2kb-Ova antibody, which are dendritic cell markers.
Figure 13B:
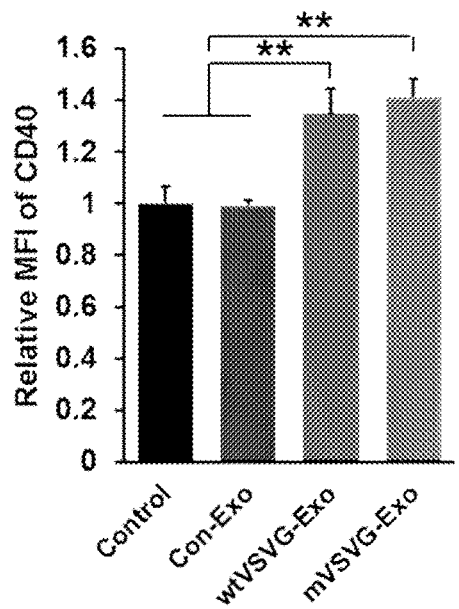
FIG. 13b is a graph illustrating the results of flow cytometry in which the extracted tumor-draining lymph nodes were converted into single cells, and then subjected to flow cytometry analysis using an anti-CD11c antibody and an anti-CD40 antibody.
Figure 13C:
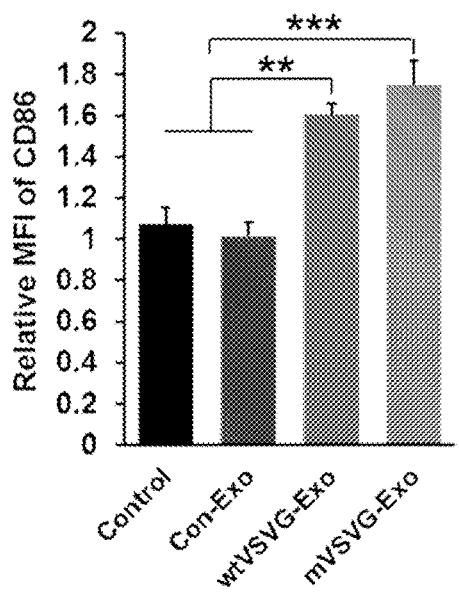
FIG. 13c is a graph illustrating the results of flow cytometry in which the extracted tumor-draining lymph nodes were converted into single cells, and then subjected to flow cytometry analysis using an anti-CD11c antibody and an anti-CD86 antibody (*: $P<0.05$; : $P<0.01$; *: $P<0.001$)
Figure 13D:
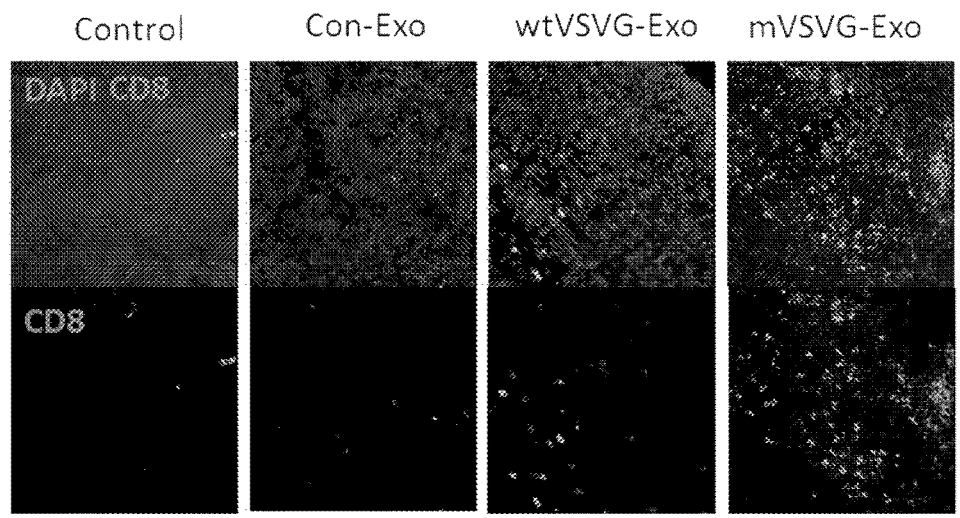
FIG. 13d shows a series of images illustrating the analysis results of the degree of infiltration of CD8 T cells in tumor tissues performed using a fluorescence microscope after staining tumor tissue slices with an anti-CD8 antibody.
Figure 13E:
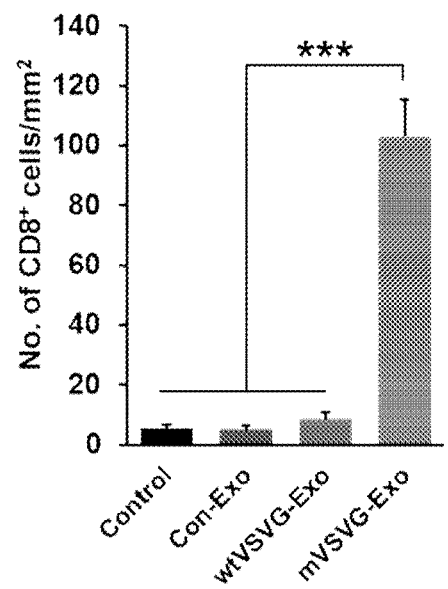
FIG. 13e is a graph illustrating the results of the quantification of the degree of infiltration of cancer tissue of CD8 T cells into cancer tissue in FIG. 13d (***: $P<0.001$).

In addition, the present inventors have conducted various analyses to determine the anticancer mechanism of the recombinant plasma membrane-based vesicle of the present invention, and as a result, have confirmed that the recombinant exosome according to an embodiment of the present invention not only can increase cancer-specific antigen presentation of dendritic cells (FIG. 13a), and promote maturation of dendritic cells (see FIGS. 13b to 13c), but also can increase the infiltration of CD8 T cells into tumor tissue (see FIGS. 13d and 13e). In addition, the present inventors have confirmed that the recombinant exosome according to an embodiment of the present invention can significantly improve the cross-sensitization ability of dendritic cells in cancer tissue (see FIG. 14a) and also has the immunological memory ability because such a cancer-specific immunocompetence is induced by cancer-specific antigens (see FIG. 14b).

Figure 15A:
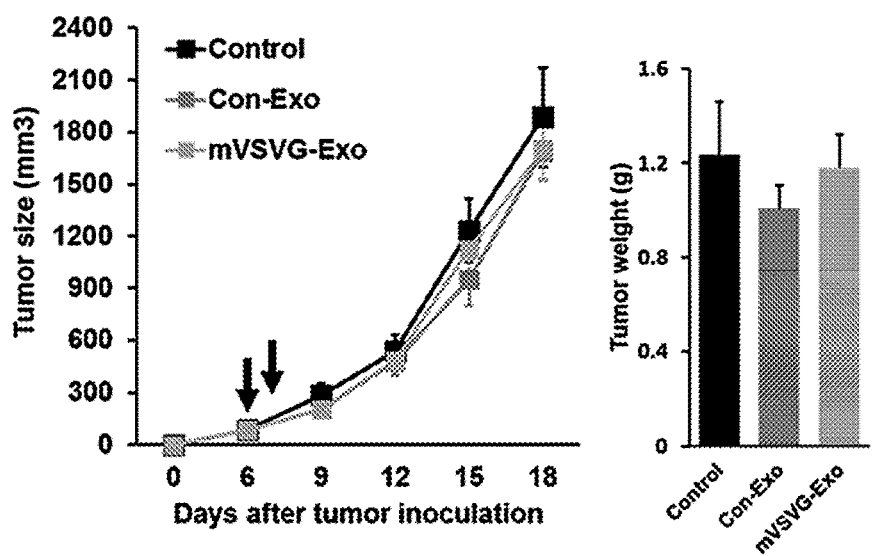
FIGS. 15a and 15b show a graph (left) illustrating the measurement results, in which a recombinant exosome including the mVSV-G (mVSVG-Exo) according to an embodiment of the present invention, a control group exosome (Con-Exo), and PBS as the control group were administered into tumor tissues of nude mice, in which cancer was induced by subcutaneously injecting EL4-Ova cancer cells thereto, and the volume of tumor tissue was measured over time, and a graph (right) illustrating the measurement results, in which mice were sacrificed on the $17^{th}$ day after cancer cell injection and the weight of the extracted tumor tissues was measured.
Figure 15B:
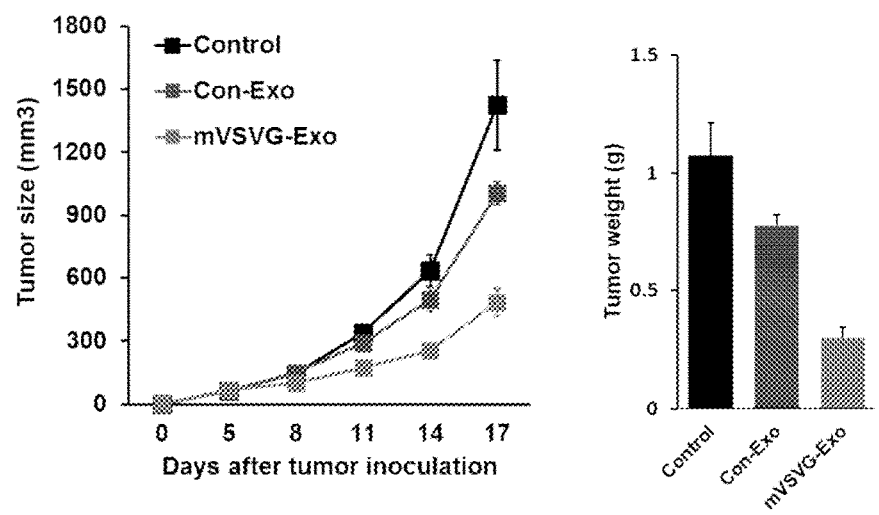

Furthermore, to determine whether the recombinant exosome according to an embodiment of the present invention is dependent on T cell immunity, the present inventors have conducted animal experiments using nude mice lacking T-cell immunity and as a result, have confirmed that the anti-cancer effect disappeared (see FIG. 15a) and that the anticancer effect appeared when the drug dose was doubled (see FIG. 15B). However, in animal experiments conducted using BATF3 knockout mice lacking CD103 and CD8 dendritic cells, which play an important role in T cell immunity, no anticancer activity was shown even in the group, in which the recombinant exosome of the present invention was administered thus confirming that the recombinant exosome according to an embodiment of the present invention exhibits an anticancer activity through dendritic cells (see FIG. 15d). To identify the role of CD8 T cells in the anticancer activity of the recombinant exosome according to an embodiment of the present invention, the present inventors have conducted animal experiments using wild-type mice in which CD8 was neutralized using an anti-CD8 antibody, and as a result, have confirmed that when the CD8 T cells were removed by administering the anti-CD8 antibody, the anticancer activity of the recombinant exosome according to an embodiment of the present invention was removed (see FIG. 15c). These results show that the recombinant exosome according to an embodiment of the present invention not only enhances the innate immune response to cancer cells by inducing the maturation of an individual's dendritic cells in a tumor microenvironment, but also enhances the acquired immune response to cancer antigens by promoting the infiltration of CD8 T cells into tumor tissue thereby exhibiting an anticancer activity.

Furthermore, the present inventors have confirmed by experiments that the recombinant exosome including a wild-type VSV-G protein, not a pH-sensitive VSV-G protein, also shows an anticancer activity by inducing T cell-specific immune responses although the effects are slightly less effective. Although it is not possible to present a viral-derived fusogenic membrane protein on the surface of cancer cells in a cancer microenvironment through the fusion of cancer cells with the recombinant exosome, the VSV-G protein itself can act as a TLR4 agonist, and thus it was confirmed that the T cell-specific immune response induced by the recombinant exosome containing the wild-type VSV-G protein in the membrane is the effect induced by activating phagocytes via binding to TLR4 receptors on phagocytes. Therefore, it can be expected that other virus-derived fusogenic membrane proteins in addition to the VSV-G protein may also be able to exhibit an effect similar to that of the wtVSVG exosome or the mVSVG exosome used in the present invention. In fact, it has been reported that a virus-derived fusogenic membrane protein (e.g., the GALV.fus protein derived from gibbon ape leukemia virus) enhances the anticancer effects of oncolytic herpes simplex virus (Fu et al., *Mol. Ther.* 7(6): 748-754, 2003).

The above results were achieved without using other anticancer agents, and it is expected that the co-administration of the recombinant exosome according to an embodiment of the present invention with other immunogenic cell death inducer(s) (e.g., doxorubicin) will show strong a synergistic effect. Therefore, the recombinant exosome according to an embodiment of the present invention is expected to be very useful for the development of a new anticancer drug that exhibits a strong anticancer activity while minimizing the side effects of the conventional anticancer agents.

In addition, although the anticancer effect was confirmed by using a recombinant exosome in an embodiment of the present invention, the plasma membrane-based vesicles derived from cells (e.g., extracellular vesicles and cell-derived nanovesicles), which are similar in structure to the recombinant exosome, are also expected to exhibit the same function as the recombinant exosome according to an embodiment of the present invention, when the host cell is transformed to include the virus-derived fusogenic membrane protein in the membrane, and then the plasma membrane-based vesicles are prepared from the transformed host cell by a conventional method (i.e., genetic recombination).

EXAMPLES

Hereinafter, the present invention will be described in more detail with reference to Examples and Experimental Examples. However, the present invention is not limited to these Examples and Experimental Examples disclosed below, but can be implemented in various forms, and the following Examples are provided to make the disclosure of the present invention complete, and to fully convey the scope of the present invention to those skilled in the art.

Example 1

Preparation of VSV-G H162R Construct

The present inventors, to prepare a recombinant exosome including a VSV-G H162R mutated protein, first prepared a gene construct encoding a H162R mutated protein, in which histidine, the $162^{nd}$ amino acid residue of VSV-G (the $178^{th}$ based on the protein disclosed in GenBank No. CAC47944), is substituted with arginine. Specifically, for this purpose, site-directed mutagenesis was performed using the plasmid DNA (pCMV-VSV-G Envelope Vector, RV-110, Cell Biolabs, abbreviated as "VSV-G construct" hereinafter), which includes the polynucleotide (SEQ ID NO: 2) encoding the wild-type VSV-G protein (SEQ ID NO: 1), as a template along with a forward primer (5'-ATA TGC CCC ACT GTC CGC AAC TCT ACA ACC TGG-3') of SEQ ID NO: 3 and a reverse primer (3'-TAT ACG GGG TGA CAG GCG TTG AGA TGT TGG ACC-5') of SEQ ID NO: 4 (the bold codes correspond to the mutated amino acid arginine).

Example 2

Preparation of Recombinant Exosome Including VSV-G H162R

The present inventors transfected the pCMV-VSV-G H162R plasmid vector (abbreviated as "VSV-G H162R construct" hereinafter, FIGS. 2a and 2b), into which the gene (SEQ ID NO: 6) encoding the VSV-G H162R protein (SEQ ID NO: 5) prepared in Example 1 above was inserted, into HEK293T cells and cultured for 48 hours. Then, the cell culture was recovered, sequentially centrifuged at 300 g for 10 minutes, at 2,000 g for 10 minutes, and at 10,000 g for 30 minutes, filtered using a 0.2 μm filter, and the pellet was recovered by ultrafiltration at 150,000 g for 3 hours (FIG. 3).

Figure 4:
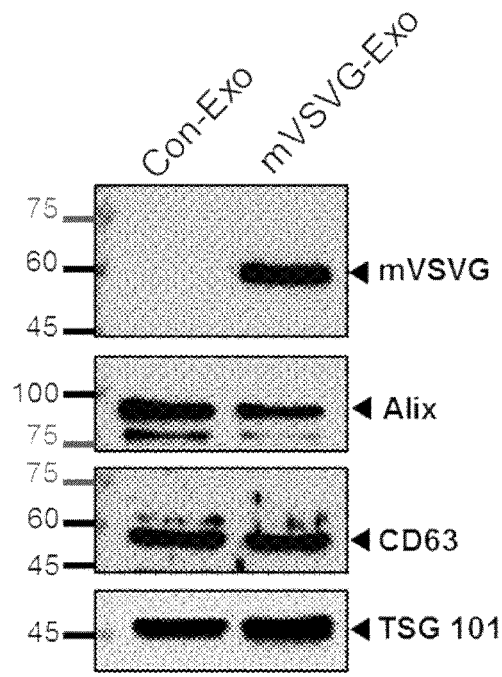
FIG. 4 shows the results of Western blot analysis of a recombinant exosome according to an embodiment of the present invention and the cell extracts transfected with the mVSV-G gene construct so as to produce the recombinant exosome.

Then, to confirm whether the VSV-G H162R mutated protein is included in the exosome, part of the recovered exosome was disrupted and Western blot analysis was performed using an anti-VSV-G antibody (Abcam, ab50549) and an anti-Alix antibody (exosome marker, Santacruz, sc99010) (FIG. 4). As a result, as illustrated in FIG. 4, the VSV-G H162R mutated protein was detected in both the transformed HEK293T cells and the recombinant exosome obtained therefrom. FIG. 4 also shows the results of Western blot analysis for Alix, CD63, and TSG 101 which are exosome markers. This means that the VSV-G H162R mutated protein is normally included in the exosome derived from the transformed cells so as to express the VSV-G H162R mutated protein according to an embodiment of the present invention.

Figure 5A:
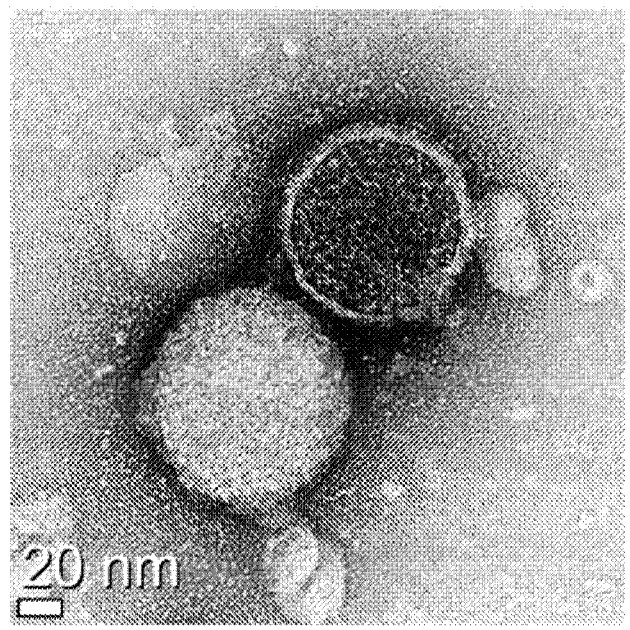
FIG. 5a is an image photographed with a transmission electron microscope of a recombinant exosome including an mVSV-G prepared according to an embodiment of the present invention.
Figure 5B:
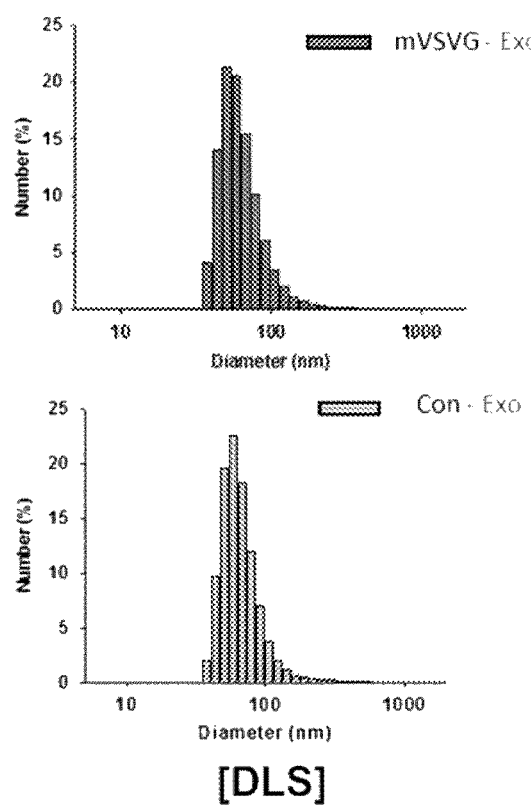
FIG. 5b shows a series of histograms illustrating analysis results of particle size of the recombinant exosome by dynamic light scattering analysis.

Subsequently, the present inventors, while photographing the recovered recombinant exosome under a transmission electron microscope (FIG. 5a), analyzed the particle size of the recombinant exosome using a dynamic light scattering (DLS) analyzer (Malvern zetasizer nano ZS, UK) (FIG. 5b). As a result, as illustrated in FIG. 5b, it was confirmed that both the recombinant exosome (mVSVG-Exo) and the control group exosome (Con-Exo) prepared according to an embodiment of the present invention have a very narrow spectrum of about 80 nm in size.

Comparative Example

Preparation of wtVSVG Exosome

The present inventors prepared, as a Comparative Example, a gene construct to express a wild-type VSV-G protein in which the $162^{nd}$ amino acid was not mutated, and then prepared a recombinant exosome (wtVSVG-Exo) in which the wild-type VSV-G protein is present in the membrane using the method of Example 2.

Example 3

Preparation of Recombinant Exosome in which Doxorubicin is Enclosed

For the loading of doxorubicin (DOX) (i.e., an immunogenic cell death inducer) to the recombinant exosome prepared in Example 2 above, purified exosomes (about $10^{11}$ exosomes) were first mixed with DOX in 1 mL PBS. Then, the DOX-recombinant exosome mixture was sonicated using the Model 505 Sonic Dismembrator with a 0.25-inch tip under the following settings: 20% amplitude, 6 cycles of 30 seconds on/off for three minutes with a two-minute cooling period between each cycle. After sonication, the Exo-DOX solution was incubated at 37° C. for 60 minutes to recover the exosomal membranes. Excess free drugs are removed by size exclusion chromatography using a NAP-10 Sephadex G25 column (GE Healthcare, Buckinghamshire, UK).

Experimental Example 1

Analysis of Presence of Fusion of VSV-G H162R into Cancer Cells Under In Vitro Conditions The present inventors attempted to determine whether the recombinant exosome prepared in Example 2 above can be fused with cancer cells in actual in vitro conditions.

Figure 6A:
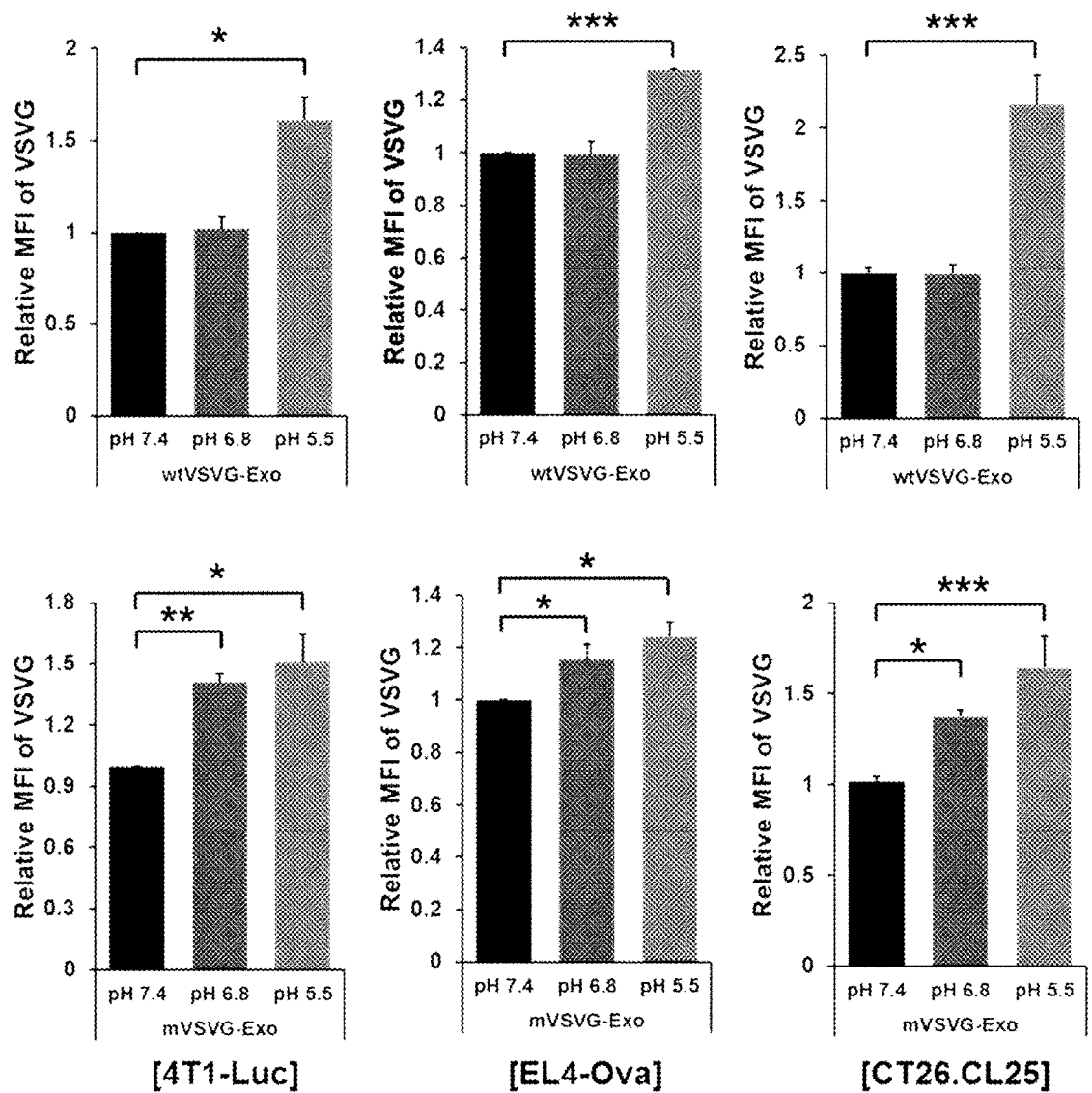
FIG. 6a shows a series of graphs illustrating the results of confirming the degree of membrane fusion with cancer cells according to pH change when three types of cancer cells (4T1-Luc, EL4-Ova, and CT26.CL25) was treated with the mVSVG-Exo according to an embodiment of the present invention (*: P<0.05; : P<0.01; *: P<0.001)

For this purpose, specifically, the present inventors added $5 \times 10^5$ cells each of the 4T1-Luc mouse breast cancer cell line, the EL4-Ova lymphoma cell line, and the CT26.CL25 colon cancer cell line to a 1 ml of fusion buffer (1.8 mM $NAH_2PO_4$, 8.4 mM $Na_2HPO_4$, 10 mM HEPES, 10 mM MES, 2.5 mM NaCl, the pH is adjusted to 7.4, 6.8, or 5.5 with HCl), performed a fusion at 37° C. for 10 minutes along with 50 μg of mVSVG-Exo or wtVSVG-Exo (the exosome prepared using the pCMV-wild-type VSVG plasmid vector), washed the resultant with a culture medium, and then stabilized in the culture medium at 37° C. for hour. In this case, the pH of the fusion buffer was divided into groups of pH 7.4, pH 6.8, or pH 5.5. Then, the degree of fusion of mVSVG-Exo or wtVSVG-Exo on the surface of cancer cells was evaluated through the anti-VSVG antibody staining using a flow cytometer. Experimental results revealed that it was possible for the wtVSVG-Exo to fuse with the surface of the cancer cell membrane, i.e., editing of the cancer cell membrane, at only pH 5.5 for all cancer cells, whereas the mVSVG was able to fuse with the surface of the cancer cell membrane not only at pH 5.5 but also at pH 6.8 of a tumor microenvironment (FIG. 6a). In addition, 4T1-Luc cells were seeded at a density of $3 \times 10^4$ cells in a 4-well chamber one day before under the same conditions, and treated with the mVSVG-Exo under the same conditions. In this case, the pH of the fusion buffer was divided into groups of pH 7.4 or pH 6.8. Then, the resultant was stained with an anti-VSVG antibody (red) and an anti-Cadherin antibody (green), which can stain cell membranes, and photographed using a confocal fluorescence microscope. As a result, it was confirmed that the mVSVG-Exo did not fuse with the surface of the cancer cell membrane at pH 7.4, but the mVSVG-Exo was able to fuse at pH 6.8 (FIG. 6b).

Figure 6C:
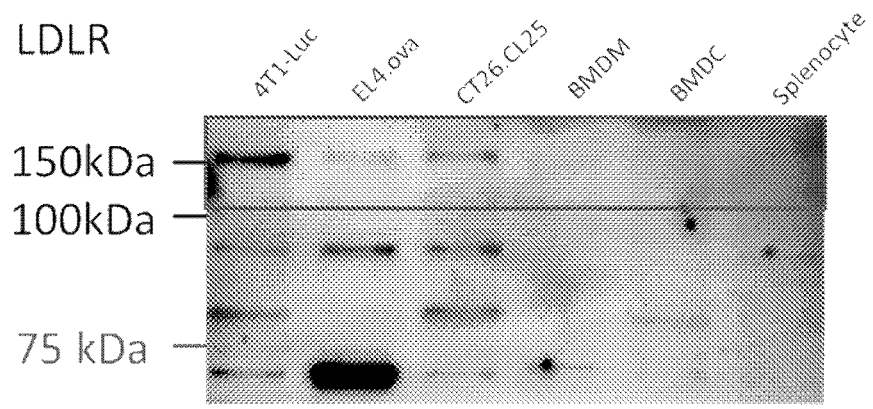
FIG. 6c shows an image illustrating the analysis results by Western blot with regard to the expression of low density lipoprotein receptors (LDLRs), which are known as VSV-G receptors, on various cell surfaces, including those of three types of cancer cells (i.e., 4T1-Luc, EL4-Ova, and CT26.CL25).

Meanwhile, a low-density lipoprotein receptor (LDLR) is most well known as a receptor of a cell membrane, to which VSVG binds to fuse with the cell membrane. As such, the present inventors examined the degree of LDLR expression by Western blot analysis using an anti-LDLR antibody against various cells including cancer cells, with which the recombinant exosome according to an embodiment of the present invention fuses. As a result, as seen in FIG. 6c, it was confirmed that LDLR was not expressed in normal cells (e.g., bone marrow-derived macrophages, bone marrow-derived dendritic cells, and spleen cells), whereas LDLR was expressed in cancer cells (e.g., 4T1-Luc, EL4-Ova, and CT26.CL25), and these results suggest that the prepared mVSVG-Exo is fused by targeting only cancer cells (FIG. 6c).

Experimental Example 2

Whether Recombinant Exosome Promotes Fusion Between Cancer Cells

Figure 7A:
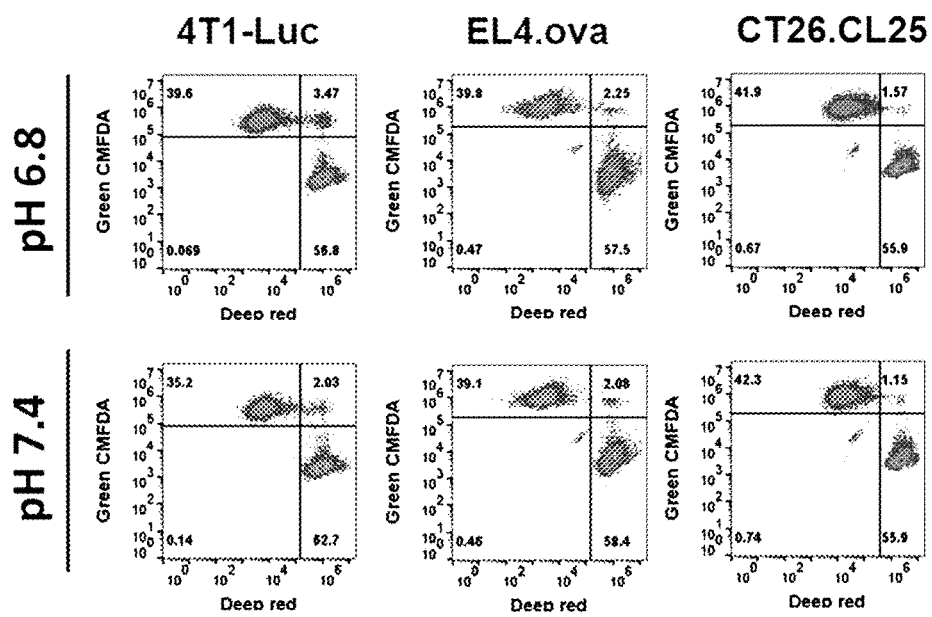
FIG. 7a shows a series of histograms illustrating the results of flow cytometry, to observe whether the mVSVG-Exo according to an embodiment of the present invention, after the fusion with three types of cancer cells (4T1-Luc, EL4-Ova, and CT26.CL25) on their surfaces, promoted fusions between the cancer cells according to pH change.
Figure 7B:
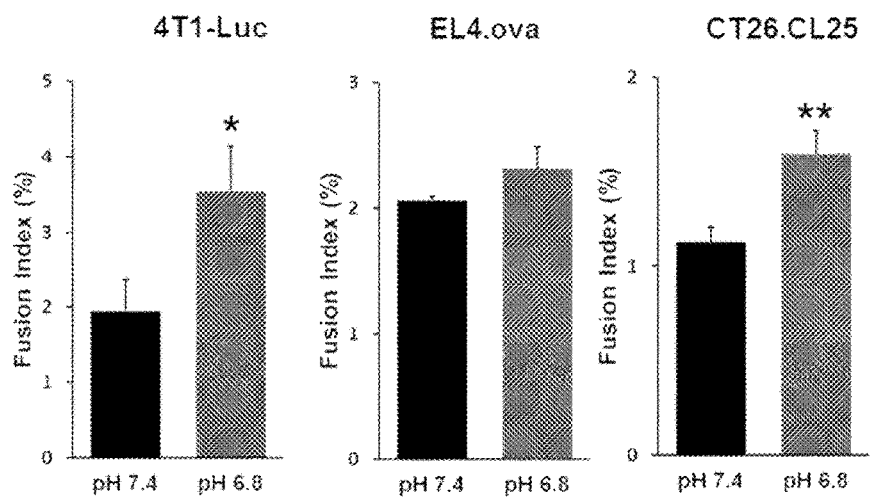

Then, the present inventors attempted to confirm whether the mVSVG-Exo promotes the fusion between cancer cells after being fused to the surface of cancer cells. For this purpose, specifically, the present inventors stained $5 \times 10^5$ cells each of the 4T1-Luc (i.e., breast cancer cell line), the EL4-Ova (i.e., lymphoma cell line), and the CT26.CL25 (i.e., colon cancer cell line) with Deep red (1 µM) or Green CMFDA (1 µM), and treated with mVSVG-Exo as described in Experimental Example 1 above to perform a fusion under the conditions of pH 7.4 or pH 6.8. Then, 24 hours after seeding each of the resultants in a 35 mm culture dish, the degree of cancer cell fusion (Green CMFDA Signal, Deep red signal double positive cell) was examined by flow cytometry. As a result, as seen in FIGS. 7a and 7b, it was confirmed that in the case of 4T1-Luc and CT26.CL25, the intercellular fusion was promoted at pH 6.8 rather than pH 7.4 by the presence of mVSVG-Exo, and even in the case of EL4-Ova, although not significant, the fusion tended to increase.

Figure 7C:
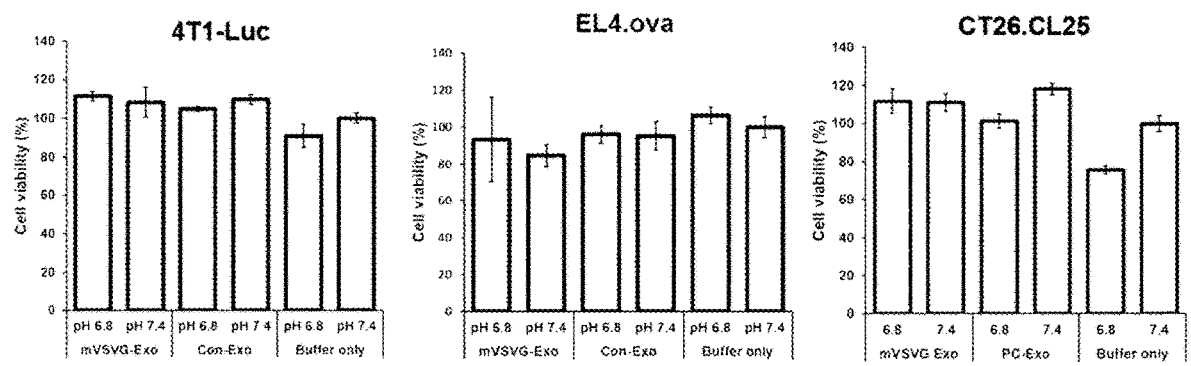
FIG. 7c shows a series of graphs illustrating the results of cell viability analysis to confirm whether the mVSVG-Exo according to an embodiment of the present invention directly induces death of cancer cells (4T1-Luc, EL4-Ova, and CT26.CL25) (*: P<0.05; **: P<0.01).

Then, the present inventors examined whether the mVSVG-Exo itself induces death of cancer cells. For this purpose, specifically, the present inventors performed fusions for the 4T1-Luc (i.e., breast cancer cell line), the EL4-Ova (i.e., lymphoma cell line), and the CT26.CL25 (i.e., colon cancer cell line) by treating each of them with the mVSVG-Exo, the control group exosome (Con-Exo), or a buffer (treatment only with a fusion buffer without an exosome) using a fusion buffer at pH 7.4 or pH 6.8, as described in Experimental Example 1 above. Thereafter, $5 \times 10^3$ cells were seeded in a 96-well plate with a normal medium in each group, and after 24 hours, cell viability was measured by CCK analysis. As a result, as seen in FIG. 7c, there was no difference in cell viability in all of the experimental groups, which suggests that the mVSVG-Exo does not directly induce the death of cancer cells.

Experimental Example 3

Analysis of Phagocytosis on Cancer Cells

The present inventors performed a phagocytosis analysis to confirm whether the fusogenic exosome according to an embodiment of the present invention promotes phagocytosis of cancer cells by macrophages and dendritic cells.

Figure 8A:
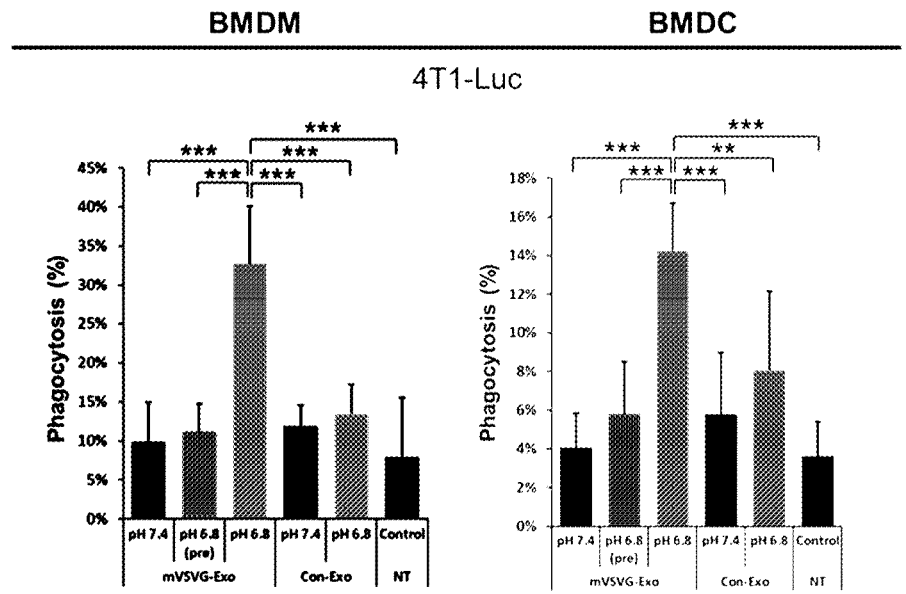
FIG. 8a shows a series of graphs illustrating the quantification of the analysis results of fluorescence microscopic images, in which the effects of the recombinant exosome including the mVSV-G according to an embodiment of the present invention and the control exosome (Con-Exo) on the phagocytic action by macrophages and dendritic cells exerted on 4T1-Luc breast cancer cells were analyzed.
Figure 8B:
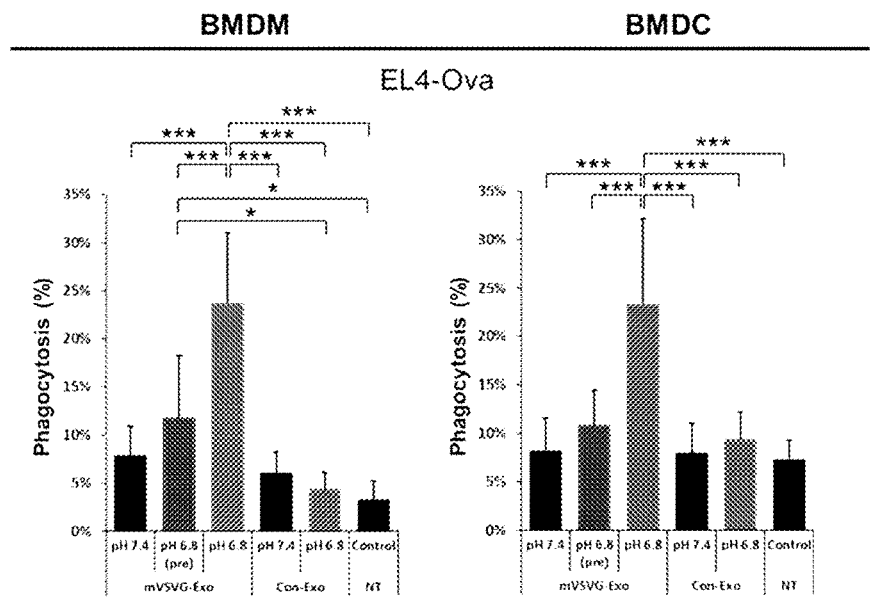
FIG. 8b shows a series of graphs illustrating the quantification of the analysis results of fluorescence microscopic images, in which the effects of the recombinant exosome including the mVSV-G according to an embodiment of the present invention and the control exosome (Con-Exo) on the phagocytic action by macrophages and dendritic cells exerted on EL4-Ova lymphoma cells were analyzed.
Figure 8C:
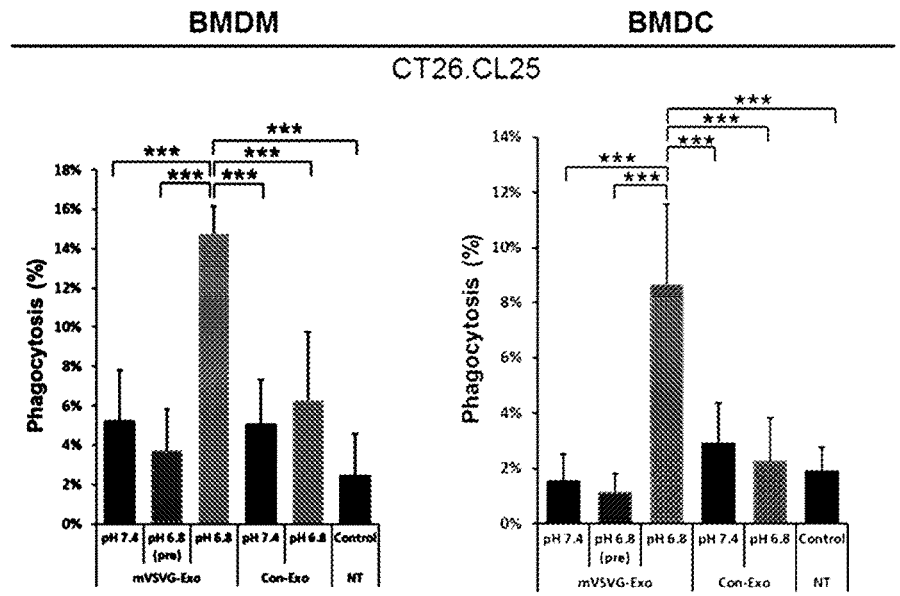
FIG. 8c shows a series of graphs illustrating the quantification of the analysis results of fluorescence microscopic images, in which the effects of the recombinant exosome including the mVSV-G according to an embodiment of the present invention and the control exosome (Con-Exo) on the phagocytic action by macrophages and dendritic cells exerted on CT46.CL25 colon cancer cells were analyzed (*: $P<0.05$; : $P<0.01$; *: $P<0.001$).

Specifically, the present inventors performed fusions for the 4T1-Luc (i.e., breast cancer cell line), the EL4-Ova (i.e., lymphoma cell line), and the CT26.CL25 (i.e., colon cancer cell line) by treating each of them with the mVSVG-Exo, the control group exosome (Con-Exo), or a buffer (treatment only with a fusion buffer without an exosome) using a fusion buffer at pH 7.4 or pH 6.8, as described in Experimental Example 1 above. After editing the membranes of the cancer cells, the cancer cells were stained with pH rodo SE 120 ng/ml. The bone marrow-derived macrophages and bone marrow-derived dendritic cells stained with Green CMFDA (1 µM) and the cancer cells stained with pH rodo SE were co-cultured at a 1:2 ratio for 2 hours. Then, the degree of phagocytosis of cancer cells by macrophages and dendritic cells was confirmed using a fluorescence microscope. As a result of the experiments as seen in FIGS. 8a to 8c, unlike other groups, only the mVSVG-Exo-treated group, in which the membranes of cancer cells were edited at pH 6.8, showed an increase of cancer cell phagocytosis by the bone marrow-derived macrophages and the bone marrow-derived dendritic cells. In addition, since the enhanced phagocytosis disappeared in the case of preblocking using an anti-VSVG antibody (marked as "pre" on the graph) after editing cancer cell membranes using the mVSVG-Exo at pH 6.8, it was confirmed that the phagocytosis-enhancing effect of the recombinant exosome according to an embodiment of the present invention is dependent on mVSVG.

This suggests that the fusogenic exosome of the present invention exhibits an anti-cancer activity based on multiple functions of performing anti-cancer actions by promoting not only fusion of cancer cells but also phagocytosis on cancer cells by macrophages and dendritic cells.

Experimental Example 4

Figure 9:
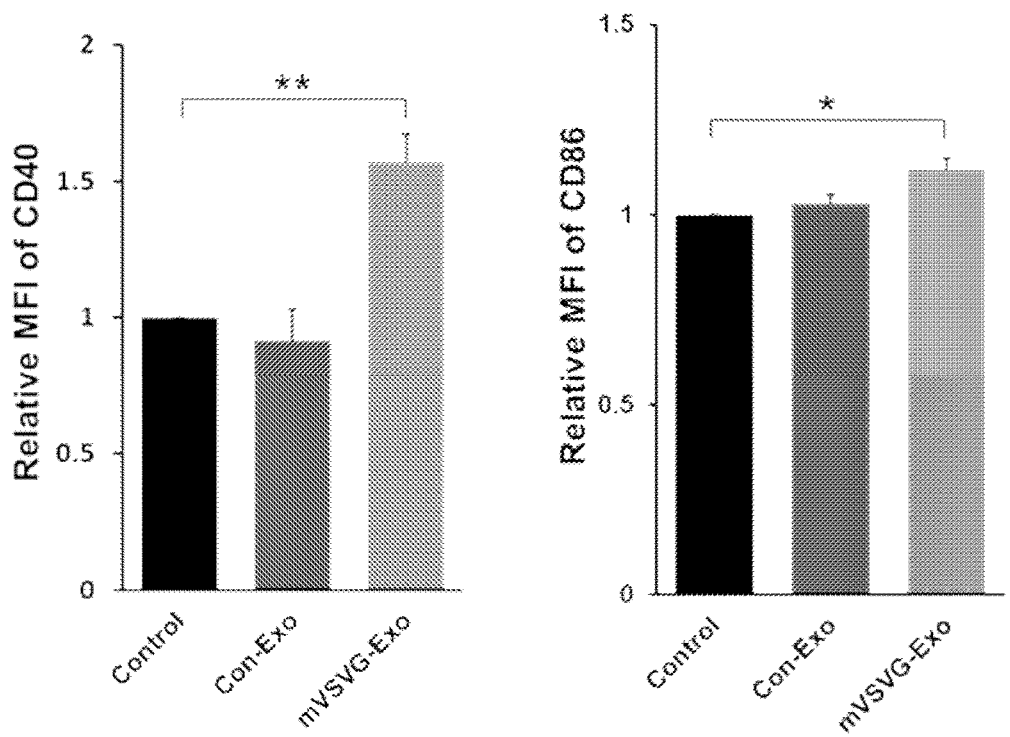
FIG. 9 shows a series of graphs in which, to examine whether VSVG can act as a TLR4 agonist and activate the functions of dendritic cells, the recombinant exosome including the mVSV-G (mVSVG-Exo) according to an embodiment of the present invention and the control group exosome (Con-Exo) were treated to bone marrow-derived dendritic cells, respectively, and the change in the relative expression rate of CD40 (left) and CD86 (right) in the bone marrow-derived dendritic cells were recorded (*: $P<0.05$; **: $P<0.01$).

Identification of Mechanism of Promoting Dendritic Cell Maturation by Recombinant Exosome VSV-G protein is known as a TLR4 agonist. As such, the present inventors examined whether the recombinant exosome according to an embodiment of the present invention promotes the maturation of dendritic cells through the TLR4 pathway. For this purpose, specifically, bone marrow-derived dendritic cells ($1 \times 10^6$ cells) were seeded in a 6-well culture dish and treated with 500 ng of mVSVG-Exo or 500 ng of Con-Exo for 24 hours. Then, the cells were collected and centrifuged, stained using an anti-CD40 and an anti-CD86 antibodies that reflect dendritic cell maturation, and then the maturation of dendritic cells was evaluated by flow cytometry. As a result of the experiments as seen in FIG. 9, it was confirmed that the mVSVG-Exo increases the level of CD40 and CD86 expressions in dendritic cells, which means that the mVSVG-Exo can promote the maturation of dendritic cells.

Experimental Example 5

Analysis of In Vivo Anticancer Effect

The present inventors examined whether the recombinant exosome according to an embodiment of the present invention can inhibit the growth of cancer cells under in vivo conditions from the results of Experimental Examples 1 to 4 above.

Figure 10A:
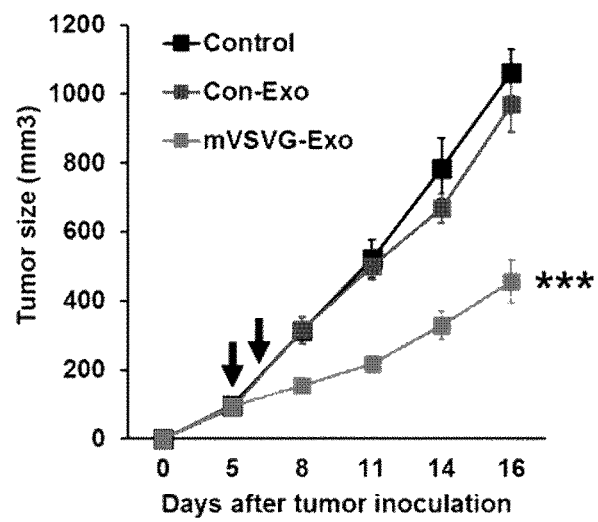
FIG. 10a is a graph comparing the size of cancer cells over time in 4T1-Luc breast cancer tumor model animals (Balb/c, 7-week-old female mice), in which the recombinant exosome (200 μg) including the mVSV-G according to an embodiment of the present invention was administered (a square represents a control group, a circle represents a control group exosome excluding the mVSV-G, and a triangle represents a recombinant exosome including the mVSV-G according to an embodiment of the present invention)
Figure 10B:
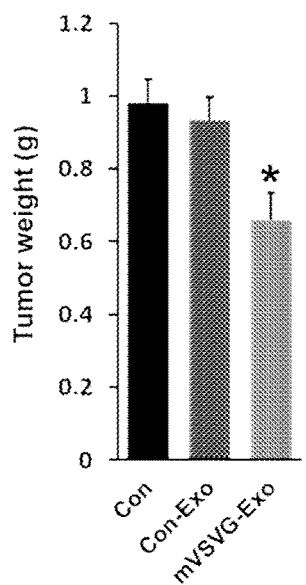
Figure 10C:
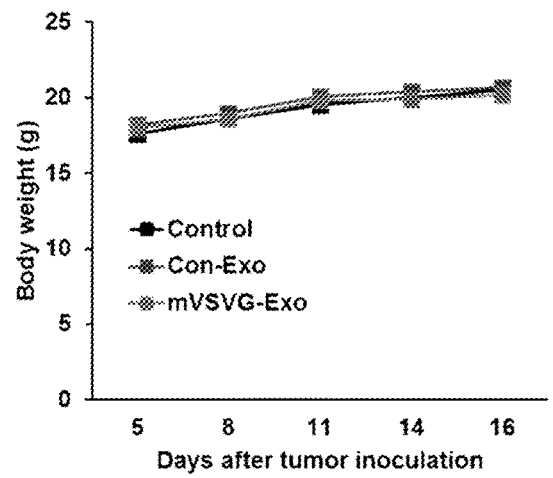
FIG. 10c is a graph illustrating the change in the weight of the animals used in the experiment illustrating (*: $P<0.05$; : $P<0.01$; *: $P<0.001$).

Specifically, the present inventors inoculated cancer cells to 7-week-old Balb/c wild-type mice (females, n=21), in which cancer was induced by subcutaneous inoculation (day 0) on the back, and injected 100 μg of the recombinant exosome (mVSVG-Exo) obtained from Example 2 above or the control group exosome (Con-Exo) into the tumor on the $5^{th}$ day and the $6^{th}$ day after the inoculation. In this case, only PBS was administered to the control group. Then, the size of the cancer tissue and the weight of the experimental animals were examined until the $16^{th}$ day after the cancer cell inoculation at 3 day intervals (FIGS. 10a and 10c). In addition, 16 days after the cancer cell inoculation, all of the experimental animals were sacrificed and the cancer tissues were extracted therefrom and weighed (FIG. 10b).

Figure 11A:
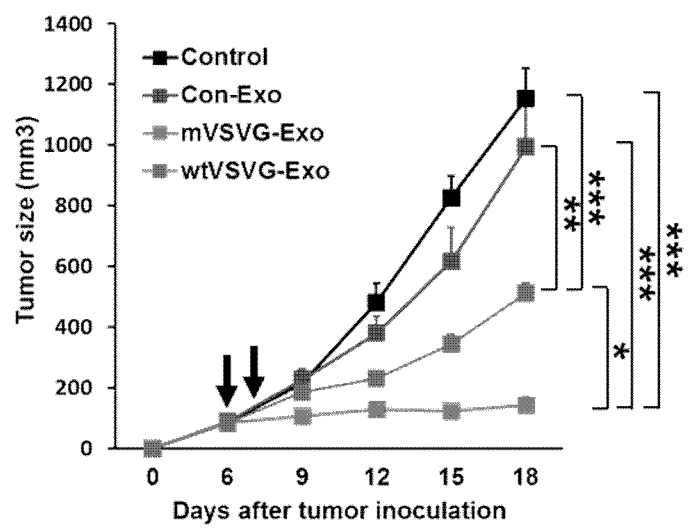
FIG. 11a is a graph illustrating the comparison of the size of cancer cells over time in EL4-Ova lymphoma tumor model animals (C57BL/6, 7-week-old female mice), in which the recombinant exosome (200 μg) including the mVSV-G according to an embodiment of the present invention was administered (a square represents a control group, a circle represents a control group exosome excluding the mVSV-G, and a triangle represents a recombinant exosome including the mVSV-G according to an embodiment of the present invention)
Figure 11B:
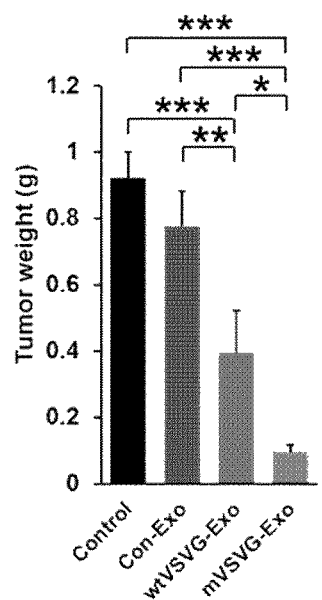
Figure 11C:
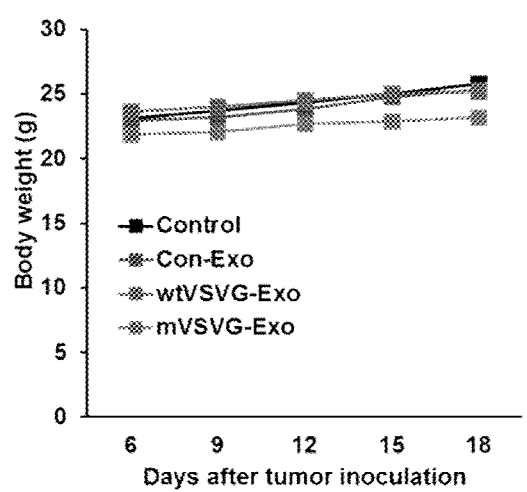
FIG. 11c is a graph illustrating the change in the weight of the animals used in the experiment (*: $P<0.05$; : $P<0.01$; *: $P<0.001$).

Moreover, the present inventors subcutaneously inoculated EL4-Ova cancer cells ($1 \times 10^6$ cells) on the left side of the back of C57BL/6 wild-type mice (day 0) to induce cancer, and then, administered wtVSVG-Exo (100 μg), mVSVG-Exo (100 μg), Con-Exo (100 μg), which are comparative groups, or PBS into the tumor by injection on the $6^{th}$ day and the $7^{th}$ day after the cancer cell inoculation. Cancer size and weight of experimental animals were measured at 3 day intervals (FIGS. 11a and 11c), and the mice were sacrificed on the $18^{th}$ day after the cancer cell injection, and the cancer tissues were extracted therefrom, and the weight of the cancer tissues was measured (FIG. 11b).

As a result of the experiments as seen in FIG. 10a to 11c, it was confirmed that the wtVSVG-Exo administered group and the mVSVG-Exo administered group, which are comparative groups, showed significant anti-cancer effects compared with the control group, and in particular, the most effective anticancer effect was observed in the mVSVG-Exo group compared with other groups.

Experimental Example 6

Correlation Between Anticancer Activity and Introduced VSV-G

Figure 12:
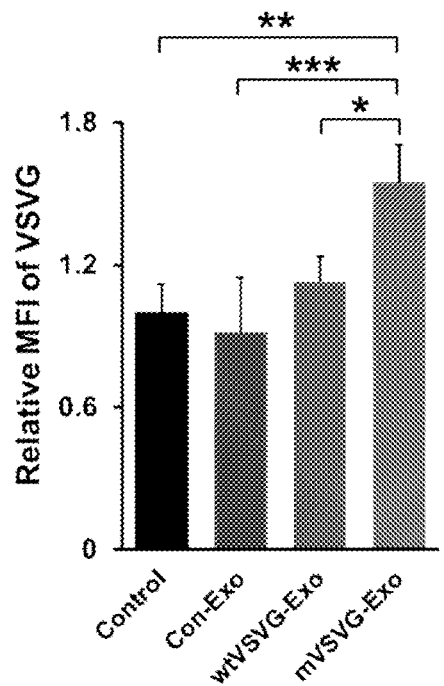
FIG. 12 is a graph illustrating the results of flow cytometry, in which a recombinant exosome including the mVSV-G (mVSVG-Exo) according to an embodiment of the present invention, a recombinant exosome including the wild-type VSV-G (wtVSVG-Exo), a control group exosome (Con-Exo) and PBS as the control group were administered into the cancer tissues of tumor model animals (EL4-Ova-injected C57BL/6 mice), and the extracted cancer tissues were converted into single cells, stained with an anti-VSV-G antibody, and then subjected to flow cytometry analysis (*: $P<0.05$; : $P<0.01$; *: $P<0.001$).

The present inventors examined the expression level of VSVG proteins on the surface of tumor cells to determine whether the in vivo anticancer effect of the recombinant exosome according to an embodiment of the present invention shown in Experimental Example 5 is due to the mVSV-G protein introduced into the exosome. For this purpose, specifically, the present inventors subcutaneously injected EL4-Ova cancer cells ($1 \times 10^6$ cells) into the left side of the back of C57BL/6 wild-type mice to induce cancer, and when the tumor size reached 100 mm$^3$ after the cancer cell injection, administered wtVSVG-Exo (100 μg), mVSVG-Exo (100 μg), Con-Exo (100 μg), or PBS into the tumor by injection. Two hours after the administration, cancer tissues were extracted therefrom and converted into single cells, and flow cytometry accompanied with staining using an anti-VSVG antibody was performed (FIG. 12). As a result of the experiments as illustrated in FIG. 12, it was confirmed that the VSVG was expressed on the surface of cancer cell membrane only in the mVSVG-Exo group.

These results confirm that the in vivo anticancer activity of the recombinant exosome according to an embodiment of the present invention is caused by the transfer of the VSVG protein into the cancer cell membrane, the VSV-G protein being present in the exosomal membrane, by the fusion of cancer cells and the recombinant exosome in a tumor microenvironment.

Experimental Example 7

Study on Anticancer Mechanism of Recombinant Exosome 7-1: Examination of Effects on Dendritic Cells The present inventors examined whether the recombinant exosome according to an embodiment of the present invention exhibits an anticancer activity by activating the functions of dendritic cells. For this purpose, specifically, the present inventors subcutaneously injected EL4-Ova cancer cells ($1 \times 10^6$ cells) on the left side of the back of C57BL/6 wild-type mice (day 0) to induce cancer, and then, administered wtVSVG-Exo (100 μg), mVSVG-Exo (100 μg), Con-Exo (100 μg), or PBS into the tumor on the $6^{th}$ day (the day of cancer cell injection is set as day 0) and the $7^{th}$ day of cancer cell injection. On the $18^{th}$ day after the cancer cell injection, mice were sacrificed to extract cancer tissue and tumor-draining lymph nodes. Then, to analyze the degree of cancer antigen presentation of dendritic cells, the tumor-draining lymph nodes which were converted into single cells were stained with an anti-CD11c antibody (i.e., a marker for dendritic cells) and an anti-H2Kb-Ova antibody (which can measure the loading of ovalbumin (i.e., a cancer-specific antigen) on MHC-1), and then analyzed by flow cytometry (FIG. 13a). As a result, as seen in FIG. 13a, the mVSVG-Exo administered group showed the best cancer-specific antigen presentation of dendritic cells. In addition, to analyze the degree of maturation of dendritic cells, single-celled tumor-draining lymph nodes were stained with an anti-CD11c antibody (i.e., a marker for dendritic cells), an anti-CD40 antibody and an anti-CD86 antibody (which can evaluate the degree of maturation of dendritic cells), respectively, and then analyzed by flow cytometry (FIGS. 13b and 13c). Experimental results showed that both wtVSVG-Exo and mVSVG-Exo groups can promote dendritic cell maturation. Therefore, it could be confirmed that the effect of promoting the dendritic cell functions of the recombinant exosome according to an embodiment of the present invention is due to the function of VSVG itself, which is not associated with the fusion of the recombinant exosome with cancer cells.

7-2: Examination of Effects of CD8 T Cells on Infiltration into Cancer Tissue

The present inventors examined the effects of the recombinant exosome according to an embodiment of the present invention on the infiltration of CD8 T cells into cancer tissue. For this purpose, specifically, the cancer tissue extracted from the experimental animal of Experimental Example 7-1 was embedded in the OCT compound and then frozen sections were prepared, which were stained with an anti-CD8 antibody and the degree of CD8 T cell invasion in cancer tissue was analyzed by a fluorescence microscope (FIGS. 13d and 13e). As a result, the mVSVG-Exo administered group showed the best degree of CD8 T cell infiltration. In particular, since the wtVSVG-Exo administered group showed no difference compared with the control group or the control exosome administered group, it was confirmed that the activity of promoting the CD8 T cell infiltration of the recombinant exosome according to an embodiment of the present invention was due to the effect of not only the function of the VSVG itself, but also the fusion of the recombinant exosome with cancer cells in a tumor microenvironment.

7-3: Analysis of Cross-Prime Ability

Figure 14A:
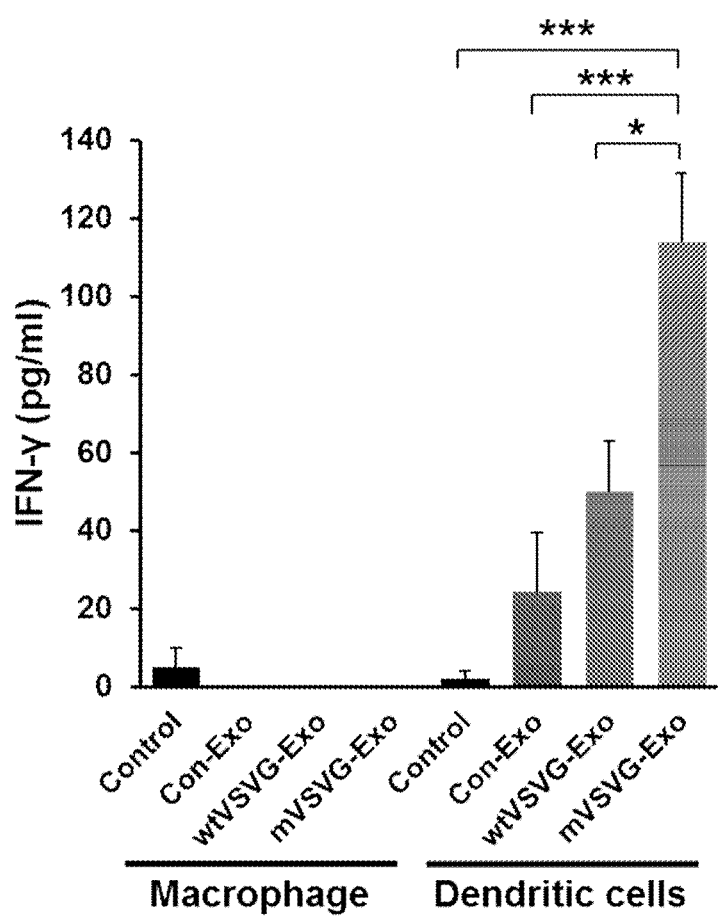
FIG. 14a is a graph illustrating the results of analysis, in which a recombinant exosome including the mVSV-G (mVSVG-Exo) according to an embodiment of the present invention, a recombinant exosome including the wild-type VSV-G (wtVSVG-Exo), a control group exosome (Con-Exo), and PBS as the control group were administered into the cancer tissues of tumor model animals (EL4-Ova-injected C57BL/6 mice), and CD11c-positive dendritic cells and F4/80-positive macrophages were isolated from the extracted tumor tissue and co-cultured with OT-1 CD8 T cells isolated from the spleens of OT-1 transgenic mice at a 1:5 ratio, respectively, and the expression level of INF-γ of the culture medium was analyzed by ELISA assay.

The present inventors examined whether the recombinant exosome according to an embodiment of the present invention has a cross-prime ability to CD8 T cells. For this purpose, specifically, the present inventors subcutaneously injected EL4-Ova cancer cells ($1\times10^6$ cells) on the left side of the back of C57BL/6 wild-type mice (day 0) to induce cancer, and then, administered wtVSVG-Exo (100 μg), mVSVG-Exo (100 μg), Con-Exo (100 μg), or PBS into the tumor on the $6^{th}$ day (the day of cancer cell injection is set as day 0) and the $7^{th}$ day of cancer cell injection. On the $18^{th}$ day after the cancer cell injection, mice were sacrificed to extract cancer tissue and spleen tissues. Then, to evaluate the cross-prime ability of macrophages and dendritic cells, dendritic cells (CD11c-positive cells) and macrophages (F4/80-positive cells) were isolated from single-celled cancer tissues using F4/80 or CD11c magnetic particles. Then, OT-1 CD8 T cells were isolated from the spleens of OT-1 transgenic mice having OT-1 CD8 T cells capable of recognizing ovalbumin loaded on MHC1 using a CD8 T cell column, and the dendritic cells or macrophages, which were isolated from cancer tissues, and the OT-1 CD8 T cells were co-cultured in a culture medium at a 1:5 ratio for 3 days, respectively. After 3 days, the medium was recovered, and the expression level of INF-γ for each group was analyzed by ELISA assay using an anti-IFN-γ antibody (FIG. 14a). As a result, it was confirmed that the cross-prime ability of the dendritic cells extracted from the cancer tissue of the mVSVG-Exo-treated mice was significantly improved, compared to those of other groups.

7-4: Examination of Immune Memory Ability

Figure 14B:
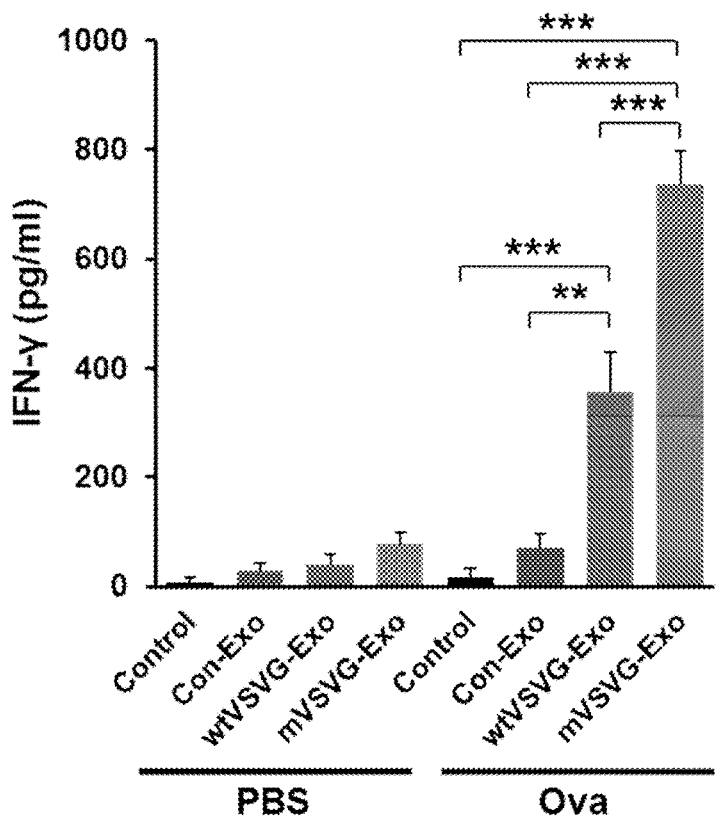
FIG. 14b is a graph illustrating the results of analysis, in which the splenocytes, in which the spleen tissues extracted from the experimental animals were converted into single cells, were treated with PBS as the control group and ovalbumin (10 μg/ml) (i.e., a cancer-specific antigen) for 24 hours, and then the expression level of INF-γ of the culture medium was analyzed by ELISA assay (*: $P<0.05$; : $P<0.01$; *: $P<0.001$).

The present inventors examined whether the recombinant exosome according to an embodiment of the present invention can trigger cancer-specific immune responses by remembering cancer antigens when the same cancer recurs after cancer treatment is completed. For this purpose, the spleen tissues extracted from the experimental animals of Experimental Example 7-3 above were converted into single cells, and $5\times10^6$ of the single cells were seeded in a 12 well culture dish along with a culture medium (1 ml) and treated with PBS or ovalbumin (10 μg/ml), which is a cancer-specific antigen, for 24 hours. Then, the medium was recovered and the expression of IFN-γ in the medium was analyzed for each group by performing ELISA assay using an anti-IFN-γ antibody (FIG. 14b). As a result, as seen in FIG. 14b, significant cancer antigen-specific immune responses were increased in the wtVSVG-Exo administered group and the mVSVG-Exo administered group, and in particular, the best cancer antigen specific immune response was observed in the mVSVG-Exo administered group.

7-5: Identification of Immune Cells Associated with Anticancer Activity of Recombinant Exosome The present inventors attempted to examine what immune cells the recombinant exosome according to an embodiment of the present invention is dependent on. First, to confirm whether anti-cancer effects can also be exhibited in nude mice lacking T-cell immunity due to enhanced phagocytosis of phagocytes, the present inventors subcutaneously injected EL4-Ova cancer cells ($1\times10^6$ cells) on the left side of the back of nude mice to induce cancer, and then, administered mVSVG-Exo (100 μg), Con-Exo (100 μg), or PBS into the tumor by injection on the $6^{th}$ day (the day of cancer cell injection is set as day 0) and the $7^{th}$ day after the cancer cell injection. Cancer size was measured at 3 day intervals, and on the 18th day after the cancer cell injection, the mice were sacrificed and cancer tissues were extracted therefrom and weighed (FIG. 15a). As a result, as seen in FIG. 15a, it was confirmed that the anticancer effect of mVSVG-Exo, which appeared in the C57BL/6 mice where T cells were present, disappeared in nude mice, and from this, it can be confirmed that the anticancer effect of the recombinant exosome according to an embodiment of the present invention is dependent on T cell immunity. To confirm whether anticancer effects from the phagocytosis of phagocytes may occur in nude mice lacking T-cell immunity, the present inventors subcutaneously injected EL4-Ova cancer cells ($1\times10^6$ cells) on the left side of the back of nude mice to induce cancer, and then, administered mVSVG-Exo (100 μg), Con-Exo (100 μg), or PBS into the tumor by injection on the $5^{th}$ day (the day of cancer cell injection is set as day 0), $6^{th}$ day, the $7^{th}$ day, and the $8^{th}$ day after the cancer cell injection (the amount used is a 2-fold greater than those used in other experiments). Cancer size was measured at 3 day intervals, and on the 17th day after the cancer cell injection, the mice were sacrificed and cancer tissues were extracted therefrom and weighed (FIG. 15b). As a result, as seen in FIG. 15b, it was confirmed that when the experiment was performed by doubling the existing drug dose and at a time point with a smaller cancer size, the anticancer effect of mVSVG-Exo could also be exhibited in nude mice. This is presumably because the recombinant exosome of the present invention can induce an innate immune response by promoting the phagocytosis of phagocytes, in addition to increasing the infiltration ability of CD8 T cells.

Figure 15C:
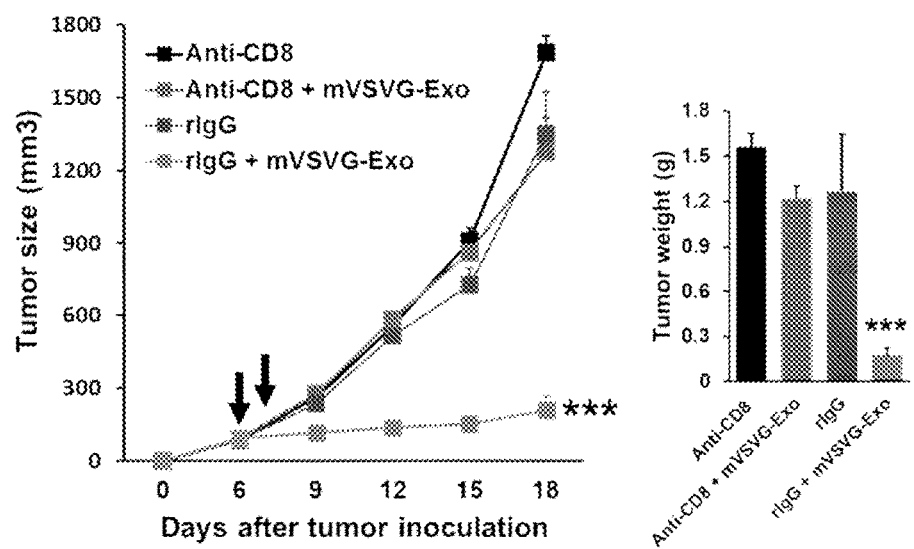
FIG. 15c shows a graph (left) illustrating the measurement results, in which a recombinant exosome including the mVSV-G (mVSVG-Exo) according to an embodiment of the present invention was administered into the tumor tissues of C57BL/6 mice, to which an anti-CD8 antibody was intraperitoneally administered at 3 day intervals starting from one day before the cancer cell injection and EL4-Ova cancer cells were injected subcutaneously so as to induce cancer, and the volume of tumor tissue over time was measured; and a graph (right) illustrating the measurement results of weight of the tumor tissues extracted from the mice sacrificed on the 18$^{th}$ day after the cancer cell injection; and a recombinant IgG was used as the control antibody (***: P<0.001).

Then, to confirm what kind of T cell immunity among T cell immunities the effect of mVSVG-Exo is dependent on, the present inventors subcutaneously injected EL4-Ova cancer cells ($1\times10^6$ cells) on the left side of the back of C57BL/6 wild-type mice to induce cancer, and then, administered mVSVG-Exo (100 μg), Con-Exo (100 μg), or PBS into the tumor by injection on the $6^{th}$ day (the day of cancer cell injection is set as day 0) and the $7^{th}$ day after the cancer cell injection. Then, to remove CD8 T cells, 150 μg of an anti-CD8 neutralizing antibody was intraperitoneally administered at 3 day intervals starting from one day before the cancer cell injection. Cancer size was measured at 3 day intervals, and on the $18^{th}$ day after the cancer cell injection, the mice were sacrificed and cancer tissues were extracted therefrom and weighed (FIG. 15c). As a result, as seen in FIG. 15c, it was confirmed that the anticancer effect of mVSVG-Exo shown in C57BL/6 mice, in which T cell immunity was retained, disappeared in the mice lacking CD8 T cells. These results suggest that the anticancer effect of mVSVG-Exo is dependent on CD8 T cell immunity.

Figure 15D:
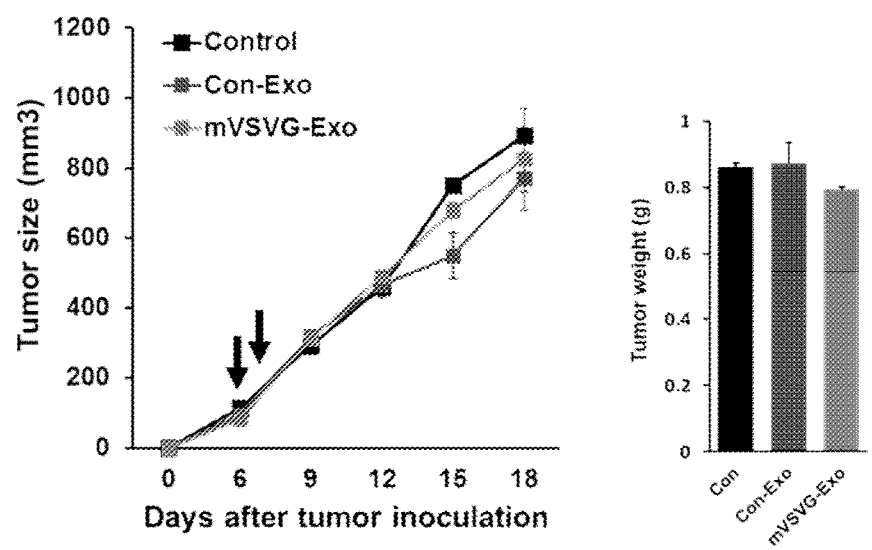
FIG. 15$d$ shows a graph (left) illustrating the measurement results, in which a recombinant exosome including the mVSV-G (mVSVG-Exo) according to an embodiment of the present invention, a control group exosome (Con-Exo), and PBS as the control group were administered into tumor tissues of BATF3 KO mice (which lack CD103 and CD8), in which cancer was induced by subcutaneous injection of EL4-Ova cancer cells, and then the volume of tumor tissue over time was measured; and a graph (right) illustrating the measurement results of weight of the tumor tissues extracted from the mice sacrificed on the 17$^{th}$ day after the cancer cell injection.

Lastly, the present inventors subcutaneously injected EL4-Ova cancer cells ($1\times10^6$ cells) on the left side of the back of BATF3 knockout mice lacking CD103 and CD8 dendritic cells, which play the most important role in forming T Cell immunity, to induce cancer, and then, administered mVSVG-Exo (100 μg), Con-Exo (100 μg), or PBS into the tumor by injection on the $6^{th}$ day (the day of cancer cell injection is set as day 0) and the $7^{th}$ day after the cancer cell injection. Cancer size was measured at 3 day intervals, and on the 18th day after the cancer cell injection, the mice were sacrificed and cancer tissues were extracted therefrom and weighed (FIG. 15d). As a result, as seen in FIG. 15d, it was confirmed that the anticancer effect of mVSVG-Exo shown in C57BL/6 mice, in which CD103 and CD8 dendritic cells were present, disappeared in the BATF3 knockout mice. These results suggest that the anticancer effect of the recombinant exosome according to an embodiment of the present invention is dependent on CD103 and CD8 dendritic cells and T cell immunity.

The above results suggest that the recombinant exosome including the VSV-G H162R mutated protein according to an embodiment of the present invention promotes a specific anticancer immune effect at the pH of a microenvironment of cancer tissue. Such an anticancer effect of the recombinant exosome including the VSV-G H162R mutated protein was achieved without the aid of other anticancer agents, and a significant synergistic effect is expected when other anticancer agents, especially immunogenic cell death inducers, are enclosed therein or co-administered with the same. In particular, when the anticancer agents are incorporated into the recombinant exosome according to an embodiment of the present invention having a membrane structure, the recombinant exosome can deliver the anticancer agents incorporated inside to the inside of cancer cells by a cancer cell-specific fusion, and thus, has an advantage in that the side effects that may occur in the anticancer agents by the actions on normal cells, can be minimized.

INDUSTRIAL APPLICABILITY

Therefore, the recombinant plasma membrane-based vesicle including the recombinant exosome according to an embodiment of the present invention not only has an anticancer activity itself, but is also expected to have a stronger anticancer activity in combination with other anticancer agents, and thus, can be very useful for the development of a novel anticancer agent that has a strong anticancer effect while minimizing side effects.

Sequence Listing Free Text

SEQ ID NO: 1 is the amino acid sequence of a wild-type VSV-G protein.

SEQ ID NO: 2 is the nucleic acid sequence of a polynucleotide encoding the wild-type VSV-G protein.

SEQ ID NO: 3 is the nucleic acid sequence of a forward primer used to clone a polynucleotide encoding the wild-type VSV-G protein.

SEQ ID NO: 4 is the nucleic acid sequence of a reverse primer used to clone a polynucleotide encoding the wild-type VSV-G protein.

SEQ ID NO: 5 is the amino acid sequence of the H162R mutated VSV-G protein according to an embodiment of the present invention.

SEQ ID NO: 6 is the nucleic acid sequence of a polynucleotide encoding the H162R mutated VSV-G protein.

SEQ ID NO: 7 is the amino acid sequence in the vicinity of the $162^{nd}$ amino acid, histidine, of the wild-type VSV-G protein.

SEQ ID NO: 8 is the amino acid sequence in the vicinity of the $162^{nd}$ amino acid, arginine, of the H162R mutated VSV-G protein.

SEQ ID NO: 9 is the nucleic acid sequence of a polynucleotide encoding a peptide in the vicinity of the $162^{nd}$ amino acid, histidine, of the wild-type VSV-G protein.

SEQ ID NO: 10 is the nucleic acid sequence of a polynucleotide encoding a peptide in the vicinity of the $162^{nd}$ amino acid, arginine, of the H162R mutated VSV-G protein.

Although the present invention has been described with reference to Examples and Experimental Examples, these are merely illustrative and will be understood by those skilled in the art that various modifications and other equivalent Examples and Experimental Examples are possible therefrom. Therefore, the true technical protection scope of the present invention will be defined by the technical spirit of the appended claims.

The invention claimed is:

1. A method of treatment comprising administering a therapeutically effective amount of a recombinant plasma membrane-based vesicle to a subject that has cancer, wherein:

(i) a vesicular stomatitis virus glycoprotein (VSV-G) mutated protein in which the 162nd amino acid, histidine, is substituted with arginine is introduced into the membrane of the vesicle and (ii) the vesicle is free of other anti-cancer agents.

2. The method of claim 1, wherein the recombinant plasma membrane-based vesicle is an exosome, extracellular vesicle, or cell-derived nanovesicle.

3. The method of claim 1, wherein the recombinant plasma membrane-based vesicle is isolated/purified from a mammalian cell, which is transformed into a gene construct comprising a polynucleotide encoding the VSV-G mutated protein and thus overexpresses the VSV-G mutated protein.

4. The method of claim 1, wherein the method further comprising administering one or more anticancer compounds.

5. The method of claim 4, wherein the anticancer compound is an immunogenic cell death inducer or an immune checkpoint inhibitor.

6. The method of claim 5, wherein the immunogenic cell death inducer is an anthracycline-type anticancer agent, a taxane-type anticancer agent, an anti-EGFR antibody, a BK channel agonist, bortezomib, cardiac glycoside, a cyclophosphamide-type anticancer agent, a GADD34/PP1 inhibitor, LV-tSMAC, measles virus, bleomycin, mitoxantrone, or oxaliplatin.

7. The method of claim 6, wherein the anthracycline-type anticancer agent is daunorubicin, doxorubicin, epirubicin, idarubicin, pixantrone, sabarubicin, or valrubicin.

8. The method of claim 6, wherein the the taxane-type anticancer agent is paclitaxel or docetaxel.

9. The method of claim 6, wherein the anti-EGFR antibody is cetuximab.

10. The method of claim 5, wherein the immune checkpoint inhibitor is a PD-1/PD-L1 interaction inhibitor or a CTLA-4/B7-1/B7-2 interaction inhibitor.

11. The method of claim 10, wherein the PD-1/PD-L1 interaction inhibitor is an antibody targeting PD-1 or PD-L1, or a functional fragment of the antibody, or a single chain-based antibody analog.

12. The method of claim 11, wherein the single chain-based antibody analog is scFv, sdAb, diabody, monobody, variable lymphocyte receptor (VLR), nanobody, or llama heavy chain antibody fragment (VHH).

13. The method of claim 11, wherein the antibody targeting PD-1 or PD-L1 is pembrolizumab, nivolumab, atezolizumab, or avelumab.

14. The method of claim 10, wherein the CTLA-4/B7-1/B7-2 interaction inhibitor is an antibody targeting CTLA-4, B7-1, or B7-2, or a functional fragment of the antibody, or a single chain-based antibody analog.

15. The method of claim 14, wherein the CTLA-4/B7-1/B7-2 interaction inhibitor is ipilimumab.

* * * * *